United States Patent
Wilkinson et al.

(10) Patent No.: US 11,384,336 B2
(45) Date of Patent: Jul. 12, 2022

(54) COMPOSITIONS AND METHODS FOR IN VITRO CULTIVATION AND/OR EXPANSION OF REGULATORY T CELLS

(71) Applicant: East Carolina University, Greenville, NC (US)

(72) Inventors: Daniel Stephen Wilkinson, Charlotte, NC (US); Mark D. Mannie, Greenville, NC (US)

(73) Assignee: East Carolina University, Greenville, NC (US)

( * ) Notice: Subject to any disclaimer, the term of this patent is extended or adjusted under 35 U.S.C. 154(b) by 299 days.

(21) Appl. No.: 16/465,773

(22) PCT Filed: Dec. 7, 2017

(86) PCT No.: PCT/US2017/065055
§ 371 (c)(1),
(2) Date: May 31, 2019

(87) PCT Pub. No.: WO2018/106885
PCT Pub. Date: Jun. 14, 2018

(65) Prior Publication Data
US 2019/0376031 A1 Dec. 12, 2019

Related U.S. Application Data

(60) Provisional application No. 62/430,991, filed on Dec. 7, 2016.

(51) Int. Cl.
| | | |
|---|---|---|
| *C12N 5/0783* | (2010.01) |
| *A61P 37/06* | (2006.01) |
| *A61K 35/17* | (2015.01) |
| *A61K 35/12* | (2015.01) |

(52) U.S. Cl.
CPC ............ *C12N 5/0637* (2013.01); *A61K 35/17* (2013.01); *A61P 37/06* (2018.01); *A61K 2035/122* (2013.01); *A61K 2035/124* (2013.01); *C12N 2501/15* (2013.01); *C12N 2501/2302* (2013.01); *C12N 2501/24* (2013.01); *C12N 2501/599* (2013.01); *C12N 2502/1114* (2013.01)

(58) Field of Classification Search
None
See application file for complete search history.

(56) References Cited

U.S. PATENT DOCUMENTS

| | | |
|---|---|---|
| 7,651,855 B2 | 1/2010 | Blazar et al. |
| 8,053,235 B2 | 11/2011 | Buckner et al. |
| 8,415,154 B2 | 4/2013 | Noelle |
| 8,562,974 B2 | 10/2013 | Battaglia et al. |
| 8,951,796 B2 | 2/2015 | Zheng et al. |
| 9,018,006 B2 | 4/2015 | Stepkowski et al. |
| 9,114,100 B2 | 8/2015 | Szabolcs |
| 9,119,807 B2 | 9/2015 | Aarvak et al. |
| 9,187,727 B2 | 11/2015 | Godfrey et al. |
| 9,213,028 B2 | 12/2015 | Roetzschke et al. |
| 9,273,282 B2 | 3/2016 | Godfrey et al. |
| 9,290,736 B2 | 3/2016 | Medof et al. |
| 9,481,866 B2 | 11/2016 | Kim et al. |
| 9,580,486 B2 | 2/2017 | Gavin et al. |
| 2004/0173778 A1 | 9/2004 | Roncarolo et al. |
| 2005/0101012 A1 | 5/2005 | Schuler et al. |
| 2006/0093580 A1 | 5/2006 | Iwashima et al. |
| 2006/0286067 A1 | 12/2006 | Horwitz et al. |
| 2007/0009497 A1 | 1/2007 | Steinman et al. |
| 2009/0010950 A1 | 1/2009 | Roncarolo et al. |
| 2009/0208471 A1 | 8/2009 | Yun |
| 2009/0257988 A1 | 10/2009 | Horwitz et al. |
| 2010/0068193 A1 | 3/2010 | Brunsvig et al. |
| 2010/0129340 A1 | 5/2010 | Rasmussen et al. |
| 2011/0014697 A1 | 1/2011 | Roetzschke et al. |
| 2011/0044902 A1 | 2/2011 | Weiner et al. |
| 2011/0123502 A1 | 5/2011 | Barry et al. |
| 2011/0268716 A1 | 11/2011 | Zheng |
| 2012/0328563 A1 | 12/2012 | Schuler et al. |
| 2013/0052642 A1 | 2/2013 | Nogueira Alvarez et al. |
| 2014/0086889 A1 | 3/2014 | Battaglia et al. |
| 2014/0348808 A1 | 11/2014 | De La Rosa |
| 2014/0377240 A1 | 12/2014 | Sitkovsky et al. |
| 2015/0210982 A1 | 7/2015 | Yun |
| 2015/0376280 A1 | 12/2015 | Ravetch |
| 2016/0194605 A1 | 7/2016 | Scott et al. |
| 2017/0081382 A1 | 3/2017 | Kannan |

(Continued)

FOREIGN PATENT DOCUMENTS

| | | |
|---|---|---|
| CN | 101603030 | 5/2011 |
| CN | 102517253 | 4/2014 |

(Continued)

OTHER PUBLICATIONS

Chaudhry et al., 2011, Immunity. vol. 24: 566-578.*
Akimova et al., 2011, PLOS one vol. 6: 1-13.*
Rosa et al., 2004, Eur. J. Immunol. vol. 34: 2480-2488.*
Gillies et al., 2006, J. Immunother vol. 29: 665.*
Zheng et al., 2007, J. Immunol. vol. 178: 2018-2027.*
Rabia et al., 2018, Blochem. Eng. J. vol. 137: 365-374.*
Antov et al. "Essential role for STAT5 signaling in CD25+CD4+ regulatory T cell homeostasis and the maintenance of self-tolerance" The Journal of Immunology, 171(7):3435-3441 (2003).

(Continued)

*Primary Examiner* — Amy E Juedes
(74) *Attorney, Agent, or Firm* — Myers Bigel, P.A.

(57) ABSTRACT

FOXP3+ regulatory T cells (Tregs) can represent powerful adoptive immunotherapies for autoimmune diseases, metabolic diseases, and other chronic inflammatory diseases. The present invention is related to the ability to maintain and expand stable Treg lines and can provide insight into FOXP3+ Treg physiology and can enable feasible strategies of Treg-based immunotherapy.

16 Claims, 11 Drawing Sheets
Specification includes a Sequence Listing.

(56) References Cited

U.S. PATENT DOCUMENTS

| | | |
|---|---|---|
| 2017/0298322 A1 | 10/2017 | Cao et al. |
| 2018/0104278 A1 | 4/2018 | Zhang et al. |

FOREIGN PATENT DOCUMENTS

| | | |
|---|---|---|
| CN | 104651309 | 5/2015 |
| CN | 103436493 | 2/2016 |
| CN | 105543171 | 5/2016 |
| CN | 104278012 | 11/2016 |
| CN | 106244539 | 12/2016 |
| CN | 104357389 | 4/2017 |
| CN | 107083360 | 8/2017 |
| CN | 107164324 | 9/2017 |
| CN | 107349219 | 11/2017 |
| EP | 1241249 | 9/2002 |
| EP | 1409650 | 4/2006 |
| EP | 2113561 | 11/2009 |
| EP | 1379625 | 6/2010 |
| EP | 2281031 | 2/2011 |
| EP | 1869163 | 9/2011 |
| EP | 2530143 | 12/2012 |
| EP | 1812563 | 4/2013 |
| EP | 2198008 | 4/2013 |
| EP | 2804625 | 11/2014 |
| EP | 1989292 | 6/2015 |
| EP | 1796474 | 2/2016 |
| EP | 3001836 | 4/2016 |
| EP | 1730260 | 5/2016 |
| JP | 5464641 | 4/2014 |
| KR | 20150126311 | 11/2015 |
| KR | 101757269 | 7/2017 |
| WO | 2006081619 | 8/2006 |
| WO | 2009037723 | 3/2009 |
| WO | 2010129770 | 11/2010 |
| WO | 2012012737 | 1/2012 |
| WO | 2012018930 | 2/2012 |
| WO | 2012143516 | 10/2012 |
| WO | 2013050596 | 4/2013 |
| WO | 2016179288 | 11/2016 |
| WO | 2017062035 | 4/2017 |
| WO | 2017072251 | 5/2017 |
| WO | 2017105265 | 6/2017 |
| WO | 2017132446 | 8/2017 |
| WO | 2018024893 | 2/2018 |
| WO | 2018024894 | 2/2018 |
| WO | 2018024896 | 2/2018 |

OTHER PUBLICATIONS

Bensinger et al. "Distinct IL-2 Receptor Signaling Pattern in CD4+ CD25+ Regulatory T Cells" The Journal of Immunology, 172(9):5287-5296 (2004).

Bluestone et al. "Type 1 diabetes immunotherapy using polyclonal regulatory T cells" Science Translational Medicine, 7(315):1-34 (2015).

Boyman et al. "Selective Stimulation of T Cell Subsets with Antibody-Cytokine Immune Complexes" Science, 311(5769):1924-1927 (2006).

Boyman et al. "The role of interleukin-2 during homeostasis and activation of the immune system" Nature Reviews Immunology, 12:180-190 (2012).

Caligiuri et al. "Tregs and Human Atherothrombotic Diseases: Toward a Clinical Application?" Arteriosclerosis, Thrombosis, and Vascular Biology, 30(9):1679-1681 (2010).

ClinicalTrials.gov "T1DM Immunotherapy Using CD4+CD127lo/-CD25+ Polyclonal Tregs (Treg)" Study Record (9 pages) (2010).

Cohen, Joe "All About Regulatory T cells (Tregs) & How to Increase Them" https://selfhacked.com/blog/treg/ (11 pages) (2019).

Couper et al. "Incomplete depletion and rapid regeneration of Foxp3+ regulatory T cells following anti-CD25 treatment in malaria-infected mice" Journal of Immunology, 178(7):4136-4146 (2007).

Dasch et al. "Monoclonal antibodies recognizing transforming growth factor-beta. Bioactivity neutralization and transforming growth factor beta 2 affinity purification" The Journal of Immunology, 142(5):1536-1541 (1989).

Huss et al. "Anti-CD25 monoclonal antibody Fc variants differentially impact regulatory T cells and immune homeostasis" Immunology, 148(3):276-286 (2016).

Huynh et al. "Control of PI(3) kinase in Treg cells maintains homeostasis and lineage stability" Nature Immunology, 16(2):188-196 (2015).

International Preliminary Report on Patentability corresponding to International Patent Application No. PCT/US2017/065055 (8 pages) (dated Jun. 20, 2019).

Kasahara et al. "Generation of allo-antigen-specific induced Treg stabilized by vitamin C treatment and its application for prevention of acute graft versus host disease model" International Immunology, 29(10):457-469 (2017).

Kraft et al. "PC61 (Anti-CD25) Treatment Inhibits Influenza A Virus-Expanded Regulatory T Cells and Severe Lung Pathology during a Subsequent Heterologous Lymphocytic Choriomeningitis Virus Infection" Journal of Virology, 87(23):12636-12647 (2013).

Leavy, Olive "Expanding TReg cell numbers in vivo" Nature Reviews Immunology, 14(10):648 (2014).

Letourneau et al. "IL-2/anti-IL-2 antibody complexes show strong biological activity by avoiding interaction with IL-2 receptor alpha subunit CD25" Proceedings of the National Academy of Sciences, 107(5):2171-2176 (2010).

Li et al. "CD4+CD25+ regulatory T-cell lines from human cord blood have functional and molecular properties of T-cell anergy" Blood, 106(9):3068-3073 (2005).

Liu et al. "Tumor Evasion of the Immune System by Converting CD4+ CD25− T Cells into CD4+ CD25+ T Regulatory Cells: Role of Tumor-Derived TGF-beta" The Journal of Immunology, 178:2883-2892 (2007).

Lowenthal et al. "High and low affinity IL 2 receptors: analysis by IL 2 dissociation rate and reactivity with monoclonal anti-receptor antibody PC61" The Journal of Immunology, 135(6):3988-3994 (1985).

Malek et al. "CD4 regulatory T cells prevent lethal autoimmunity in IL-2Rbeta-deficient mice. Implications for the nonredundant function of IL-2" Immunity, 17(2):167-178 (2002).

Malek et al. "Interleukin-2 Receptor Signaling: At the Interface between Tolerance and Immunity" Immunity, 33(2):153-165 (2010).

Maloy et al. "Fueling regulation: IL-2 keeps CD4+ Treg cells fit" Nature Immunology, 6:1071-1072 (2005).

Mannie et al. "IL-4 responsive CD4+ T cells specific for myelin basic protein: IL-2 confers a prolonged postactivation refractory phase" Immunology and Cell Biology, 81:8-19 (2003).

McHugh et al. "Paracrine co-delivery of TGF-beta and IL-2 using CD4-targeted nanoparticles for induction and maintenance of regulatory T cells" Biomaterials, 59:172-181 (2015).

Nair et al. "Vitamin C Facilitates Demethylation of the Foxp3 Enhancer in a Tet-Dependent Manner" The Journal of Immunology, 196(5):2119-2131 (2016).

Nikolouli et al. "Alloantigen-Induced Regulatory T Cells Generated in Presence of Vitamin C Display Enhanced Stability of Foxp3 Expression and Promote Skin Allograft Acceptance" Frontiers in Immunology, 8:1-12 (2017).

O'Shea et al. "Cytokines and autoimmunity" Nature Reviews Immunology, 2(1):37-45 (2002).

Rouse et al. "The Role of IL-2 in the Activation and Expansion of Regulatory T-cells and the Development of Experimental Autoimmune Encephalomyelitis" Immunobiology, 218(4):674-682 (2013).

Sadlack et al. "Ulcerative colitis-like disease in mice with a disrupted interleukin-2 gene" Cell, 75(2):253-261 (1993).

Setiady et al. "In vivo deletion of CD4+ FOXP3+ Treg cells by the PC61 anti-CD25 monoclonal antibody is mediated by FcgammaRIII+ phagocytes" European Journal of Immunology, 40:780-786 (2010).

Sharfe et al. "Human immune disorder arising from mutation of the a chain of the interleukin-2?receptor" Proceedings of the National Academy of Sciences USA, 94(7):3168-3171 (1997).

(56) References Cited

OTHER PUBLICATIONS

Someya et al. "Improvement of Foxp3 stability through CNS2 demethylation by TET enzyme induction and activation" International Immunology, 29(8):365-375 (2017).
Spangler et al. "Antibodies to Interleukin-2 elicit selective T cell subset potentiation through distinct conformational mechanisms" Immunity, 42(5):815-825 (2015).
Stephens et al. "Comment on 'Cutting Edge: Anti-CD25 Monoclonal Antibody Injection Results in the Functional Inactivation, Not Depletion, of CD4+CD25+ T Regulatory Cells'" The Journal of Immunology, 177(4):2036-2038 (2006).
Teglund et al. "Stat5a and Stat5b Proteins Have Essential and Nonessential, or Redundant, Roles in Cytokine Responses" Cell, 93:841-850 (1998).
Thome et al. "Chloroquine Treatment Enhances Regulatory T Cells and Reduces the Severity of Experimental Autoimmune Encephalomyelitis" PLoS One, 8(6):e65913 (2013).
Wang et al. "IFN-beta Facilitates Neuroantigen-Dependent Induction of CD25+ FOXP3+ Regulatory T Cells That Suppress Experimental Autoimmune Encephalomyelitis" The Journal of Immunology, 197:2992-3007 (2016).
Yue et al. "Control of Foxp3 stability through modulation of TET activity" Journal of Experimental Medicine, 213(3):377-397 (2016).
Zelenay et al. "Comment on 'Cutting Edge: Anti-CD25 Monoclonal Antibody Injection Results in the Functional Inactivation, Not Depletion, of CD4+CD25+ T Regulatory Cells'" The Journal of Immunology, 177(4):2036-2037 (2006).
Zou et al. "Overexpression of human transforming growth factor-beta1 using a recombinant CHO cell expression system" Protein Expression and Purification, 37(2):265-272 (2004).
Extended European Search Report corresponding to European Patent Application No. 17878510.1 (9 pages) (dated Apr. 2, 2020).
Ghosh et al. "Depletion of CD4+ CD25+ regulatory T cells confers susceptibility to experimental autoimmune encephalomyelitis (EAE) in GM-CSF-deficient Csf2-/-mice" Journal of Leukocyte Biology, 100:747-760 (2016).
Wilkinson et al. "Partial CD25 Antagonism Enables Dominance of Antigen-Inducible CD25high FOXP3+ Regulatory T Cells As a Basis for a Regulatory T Cell-Based Adoptive Immunotherapy" Frontiers in Immunology, 8(1782):1-21 (2017).
Dienz et al. "The effects of IL-6 on CD4 T cell responses" Clinical Immunology, 130(1):27-33 (2009).
International Search Report and the Written Opinion of the International Searching Authority corresponding to International Patent Application No. PCT/US2017/065055 (11 pages) (dated Mar. 6, 2018).
Pellerin et al. "Regulatory T cells and their roles in immune dysregulation and allergy" Journal of Immunology Research, 58:1-19 (2014).
Perdigoto et al. "Inducing and Administering Tregs to Treat Human Disease" Frontiers in Immunology, 6(654):1-13 (2016).
Smith-Garvin et al. "T Cell Activation" Annual Review of Immunology, 27:591-619 (2009).
Tato et al. "Helper T cell differentiation enters a new era: Le Roi est mort; vive le Roi!" The Journal of Experimental Medicine, 203(4):809-812 (2006).

\* cited by examiner

SEQUENCE LISTING

<160> NUMBER OF SEQ ID NOS: 7

<210> SEQ ID NO 1

-continued

<211> LENGTH: 20
<212> TYPE: DNA
<213> ORGANISM: Mus musculus

<400> SEQUENCE: 1
cacctatgcc acccttatcc                                                20

<210> SEQ ID NO 2
<211> LENGTH: 19
<212> TYPE: DNA
<213> ORGANISM: Mus musculus

<400> SEQUENCE: 2
attgtgggtc aaggggaag                                                 19

<210> SEQ ID NO 3
<211> LENGTH: 21
<212> TYPE: PRT
<213> ORGANISM: Artificial
<220> FEATURE:
<223> OTHER INFORMATION: peptide

<400> SEQUENCE: 3

Met Glu Val Gly Trp Tyr Arg Ser Pro Phe Ser Arg Val Val His Leu
1               5                   10                  15

Tyr Arg Asn Gly Lys
            20

<210> SEQ ID NO 4
<211> LENGTH: 17
<212> TYPE: PRT
<213> ORGANISM: Artificial
<220> FEATURE:
<223> OTHER INFORMATION: peptide

<400> SEQUENCE: 4

Ile Ser Gln Ala Val His Ala Ala His Ala Glu Ile Asn Glu Ala Gly
1               5                   10                  15

Arg

<210> SEQ ID NO 5
<211> LENGTH: 297
<212> TYPE: PRT
<213> ORGANISM: Artificial
<220> FEATURE:
<223> OTHER INFORMATION: PC61scFv

<400> SEQUENCE: 5

Met Ala Lys Trp Val Thr Phe Leu Leu Leu Leu Phe Ile Ser Gly Ser
1               5                   10                  15

Ala Phe Ser His His His His His His His Gln Val Val Leu
                20                  25                  30

Thr Gln Pro Lys Ser Val Ser Ala Ser Leu Glu Ser Thr Val Lys Leu
            35                  40                  45

Ser Cys Lys Leu Asn Ser Gly Asn Ile Gly Ser Tyr Tyr Met His Trp
        50                  55                  60

Tyr Gln Gln Arg Glu Gly Arg Ser Pro Thr Asn Leu Ile Tyr Arg Asp
65                  70                  75                  80

Asp Lys Arg Pro Asp Gly Ala Pro Asp Arg Phe Ser Gly Ser Ile Asp
                85                  90                  95

Ile Ser Ser Asn Ser Ala Phe Leu Thr Ile Asn Asn Val Gln Thr Glu
                100                 105                 110

```
Asp Glu Ala Met Tyr Phe Cys His Ser Tyr Asp Gly Arg Met Tyr Ile
        115                 120                 125
Phe Gly Gly Gly Thr Lys Leu Thr Val Leu Gly Gln Pro Gly Gly Gly
        130                 135                 140
Gly Ser Gly Gly Gly Ser Gly Gly Gly Ser Gly Gly Gly Gly
145                 150                 155                 160
Ser Gln Val Gln Leu Gln Gln Ser Gly Ala Glu Leu Val Arg Pro Gly
                165                 170                 175
Thr Ser Val Lys Leu Ser Cys Lys Val Ser Gly Asp Thr Ile Thr Ala
            180                 185                 190
Tyr Tyr Ile His Phe Val Lys Gln Arg Pro Gly Gln Gly Leu Glu Trp
        195                 200                 205
Ile Gly Arg Ile Asp Pro Glu Asp Asp Ser Thr Glu Tyr Ala Glu Lys
    210                 215                 220
Phe Lys Asn Lys Ala Thr Ile Thr Ala Asn Thr Ser Ser Asn Thr Ala
225                 230                 235                 240
His Leu Lys Tyr Ser Arg Leu Thr Ser Glu Asp Thr Ala Thr Tyr Phe
                245                 250                 255
Cys Thr Thr Asp Asn Met Gly Ala Thr Glu Phe Val Tyr Trp Gly Gln
            260                 265                 270
Gly Thr Leu Val Thr Val Ser Ser Ala Lys Gly Gly Gly Ser Glu Gly
        275                 280                 285
Gly Gly Ser Glu Gly Gly Gly Ser Gly
        290                 295

<210> SEQ ID NO 6
<211> LENGTH: 119
<212> TYPE: PRT
<213> ORGANISM: Artificial
<220> FEATURE:
<223> OTHER INFORMATION: PC61 variable heavy domain

<400> SEQUENCE: 6

Gln Val Gln Leu Gln Gln Ser Gly Ala Glu Leu Val Arg Pro Gly Thr
1               5                   10                  15
Ser Val Lys Leu Ser Cys Lys Val Ser Gly Asp Thr Ile Thr Ala Tyr
            20                  25                  30
Tyr Ile His Phe Val Lys Gln Arg Pro Gly Gln Gly Leu Glu Trp Ile
        35                  40                  45
Gly Arg Ile Asp Pro Glu Asp Asp Ser Thr Glu Tyr Ala Glu Lys Phe
    50                  55                  60
Lys Asn Lys Ala Thr Ile Thr Ala Asn Thr Ser Ser Asn Thr Ala His
65                  70                  75                  80
Leu Lys Tyr Ser Arg Leu Thr Ser Glu Asp Thr Ala Thr Tyr Phe Cys
                85                  90                  95
Thr Thr Asp Asn Met Gly Ala Thr Glu Phe Val Tyr Trp Gly Gln Gly
            100                 105                 110
Thr Leu Val Thr Val Ser Ser
        115

<210> SEQ ID NO 7
<211> LENGTH: 113
<212> TYPE: PRT
<213> ORGANISM: Artificial
<220> FEATURE:
<223> OTHER INFORMATION: PC61 variable light domain
```

```
<400> SEQUENCE: 7

Gln Val Val Leu Thr Gln Pro Lys Ser Val Ser Ala Ser Leu Glu Ser
1               5                   10                  15

Thr Val Lys Leu Ser Cys Lys Leu Asn Ser Gly Asn Ile Gly Ser Tyr
            20                  25                  30

Tyr Met His Trp Tyr Gln Gln Arg Glu Gly Arg Ser Pro Thr Asn Leu
        35                  40                  45

Ile Tyr Arg Asp Asp Lys Arg Pro Asp Gly Ala Pro Asp Arg Phe Ser
    50                  55                  60

Gly Ser Ile Asp Ile Ser Ser Asn Ser Ala Phe Leu Thr Ile Asn Asn
65                  70                  75                  80

Val Gln Thr Glu Asp Glu Ala Met Tyr Phe Cys His Ser Tyr Asp Gly
                85                  90                  95

Arg Met Tyr Ile Phe Gly Gly Gly Thr Lys Leu Thr Val Leu Gly Gln
                100                 105                 110

Pro
```

COMPOSITIONS AND METHODS FOR IN VITRO CULTIVATION AND/OR EXPANSION OF REGULATORY T CELLS

RELATED APPLICATION INFORMATION

This application claims the benefit of and priority to U.S. Provisional Application Ser. No. 62/430,991, filed Dec. 7, 2016, the disclosure of which is hereby incorporated by reference herein in its entirety.

STATEMENT OF GOVERNMENT SUPPORT

This invention was made with government support under Grant Nos. R15 NS075830, R01 NS072150-01A1, and R01 AI126398-01 awarded by the National Institutes of Health. The government has certain rights in the invention.

FIELD

The present invention relates to compositions and methods for activating, culturing, expanding, maintaining, and/or stabilizing the growth of regulatory T cell populations, including regulatory FOXP3$^+$ T cells.

BACKGROUND

CD4$^+$ CD25$^+$ FOXP3$^+$ regulatory T cells (Tregs) play an integral role in preventing autoimmunity and controlling inflammation. The importance of Tregs is illustrated by the fact that loss-of-function mutations in FOXP3 leads to the rapid, fatal multi-organ autoimmune disorders IPEX and scurfy in humans and mice, respectively. Moreover, dysfunctional Tregs are linked to increased susceptibility to certain autoimmune diseases such as multiple sclerosis (MS) and type 1 diabetes (T1D). Because of their suppressive capabilities, Tregs offer a unique therapeutic potential for autoimmune diseases, allergic diseases, transplant tolerance, and chronic inflammatory disorders. Treg adoptive transfer therapies, where Tregs are induced or purified ex vivo and then infused into a syngeneic organism, have shown encouraging results in animal models of autoimmune disease such as experimental autoimmune encephalomyelitis (EAE), the animal model of MS, T1D, and colitis. In early phase clinical trials, Treg adoptive transfer therapies for tissue transplantation and T1D have shown favorable outcomes, but no adoptive Treg therapy has yet to be approved as a treatment option. An additional approach to Treg-mediated therapies involves induction or expansion of Tregs in vivo through the use of tolerogenic vaccines or anti-inflammatory drugs, such as interferon-β. Interferon-β is a first-line treatment option for relapsing-remitting MS. Interferon-β has been shown to increase numbers of Tregs in circulation. Tolerogenic vaccines ideally work by inducing or expanding antigen-specific Tregs, which would leave the adaptive immune response intact.

FOXP3 is needed for adaptive self-tolerance, and FOXP3 is expressed in a canonical lineage of suppressive Tregs; however, it cannot be assumed that the role of FOXP3 in self-tolerance is entirely mediated via the expression of FOXP3 in this lineage of CD4$^+$ CD25$^+$ FOXP3$^+$ Tregs. FOXP3 may play inhibitory roles in other cell types, particularly during transient expression in canonical conventional T cell subsets. For example, FOXP3 can be transiently expressed during activation in human T cells and is expressed in quasi-stable non-committed CD25$^{low}$ FOXP3$^+$ T cells in mice. The assessment of FOXP3$^+$ Tregs requires new assessment tools to analyze this subset. One approach to assess these questions is to induce Tregs in vitro and expand/maintain in pure culture, and show via adoptive transfer experiments that these Tregs suppress EAE.

One major setback for Treg-mediated therapies is that Tregs are notoriously unstable and plastic. In vivo studies using fate-mapping techniques to track FOXP3 expression showed that under certain environmental circumstances, Tregs can lose FOXP3 expression and actually adopt an effector T cell phenotype. These so called "ex-Tregs" can potentially exacerbate autoimmune disease as FOXP3 is required for Treg suppressive activity. Ex vivo expansion and culturing of Tregs has faced many difficulties due to the fact that Tregs are relatively anergic in vitro and that contaminating FOXP3$^-$ conventional cells (Tcons) can quickly outgrow Tregs. Additional evidence shows that Tregs lose FOXP3 expression over time when cultured ex vivo. Propagation and expansion of Tregs in vitro is a step in generating the numbers of Tregs necessary for Treg adoptive transfer therapies. What drives Treg instability, especially in vitro, is not well understood.

IL-2 is involved in both the induction and maintenance of Tregs. CD25, the IL-2 receptor alpha chain, is constitutively expressed on Tregs and represents a phenotypic marker for Tregs, although CD25 is also expressed at high levels on activated effector T cells. Various therapeutic techniques manipulating IL-2 availability have met with some success in animal models and in the clinic. The rationale is that selectively expanding Tregs will alleviate autoimmune disorders. While most of the focus to date has been on manipulating IL-2 directly, little attention has focused on manipulating CD25.

FOXP3$^+$ regulatory T cells (Tregs) represent potentially powerful adoptive immunotherapies for autoimmune disease and other chronic inflammatory diseases. However, the field currently lacks reliable technologies to enable long-term in vitro expansion of stable, antigen-specific FOXP3$^+$ Treg lines. Activation of naïve T cells in the presence of TGF-β elicits the initial differentiation of the FOXP3$^+$ lineage, but these Treg lines lack phenotypic stability and rapidly convert to a Tcon phenotype during in vitro propagation in IL-2. Thus, there remains a need for improved methods of growing and maintaining Treg populations.

SUMMARY OF THE INVENTION

The present invention is related to the development of methods for preparing and/or expanding a regulatory T-cell (Treg) population. Tregs are qualitatively distinguished from Tcons and non-Tregs in that Tregs constitutively express high levels of CD25 (IL-2 receptor alpha, IL-2Rα), whereas Tcons and non-Tregs are CD25$^-$ or only transiently express an activation-dependent CD25$^{high}$ phenotype. Due to differential expression of CD25, it was reasoned that anti-CD25 mAbs would only partially block IL-2 signaling in Tregs while completely blocking IL-2 responses of Tcons, and that the differential inhibition of CD25 would enable the preferential and dominant outgrowth of Tregs during in vitro cultivation. TGF-β-induced Treg lines that were maintained in IL-2 in the presence of the anti-CD25 antibody PC61 (non-depleting mAb in vitro) maintained a FOXP3$^{high}$ phenotype during prolonged in vitro propagation (~90% FOXP3$^+$ Tregs) whereas parallel cultures lacking PC61 rapidly lost FOXP3 and reverted to a Tcon phenotype. Stable FOXP3$^{high}$ lines acquired Treg-associated markers Neuropilin-1 and Helios. These lines also exhibited antigen-specific activation and expansion in vitro in the presence of TGF-β and antigen without loss of FOXP3. When activated with myelin oligodendrocyte glycoprotein peptide fragment 35-55 (MOG35-55) and TGF-β, blastogenic FOXP3+ Tregs from MOG35-55-specific 2D2 TCR transgenic mice suppressed EAE in adoptive transfer assays. A "Treg window," marked by low IL-2 concentrations coupled with high PC61 concentrations that restricted IL-2 signaling pathways, enabled dominant stable outgrowth of suppressive FOXP3$^{high}$ Tregs. The ability to maintain and expand stable Treg lines will provide insight into FOXP3+ Treg physiology and can enable feasible strategies of Treg-based immunotherapy.

Thus, in an aspect of the present invention, provided is a method of preparing a regulatory T-cell (Treg) population including: exposing a T-cell population to a medium including an anti-inflammatory cytokine and an antibody to an anti-inflammatory cytokine receptor; and expanding the T-cell population, to provide a Treg population.

In another aspect of the present invention, provided is a Treg population, compositions including a Treg population, and pharmaceutical formulations including a Treg population prepared by methods set forth according to the present invention.

In yet another aspect of the invention, provided is a method of treating or modulating an immunological disorder in a subject in need thereof including administering a therapeutic amount of a Treg population, compositions including a Treg population, or pharmaceutical formulations including a Treg population prepared by methods set forth according to the present invention.

In yet another aspect of the invention, provided is a method of eliciting a tolerogenic response in a subject in need thereof including the step of administering a therapeutic amount of a Treg population, or a pharmaceutical formulation including a Treg population prepared by methods set forth according to the present invention.

In yet another aspect of the invention, provided is a method of maintaining a Treg population including: exposing a Treg population to a medium including an anti-inflammatory cytokine and an antibody to an anti-inflammatory cytokine receptor; and maintaining the Treg population in the medium including an anti-inflammatory cytokine and an antibody to an anti-inflammatory cytokine receptor.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the example embodiments that follow, such description being merely illustrative of the present invention.

Figure 11:
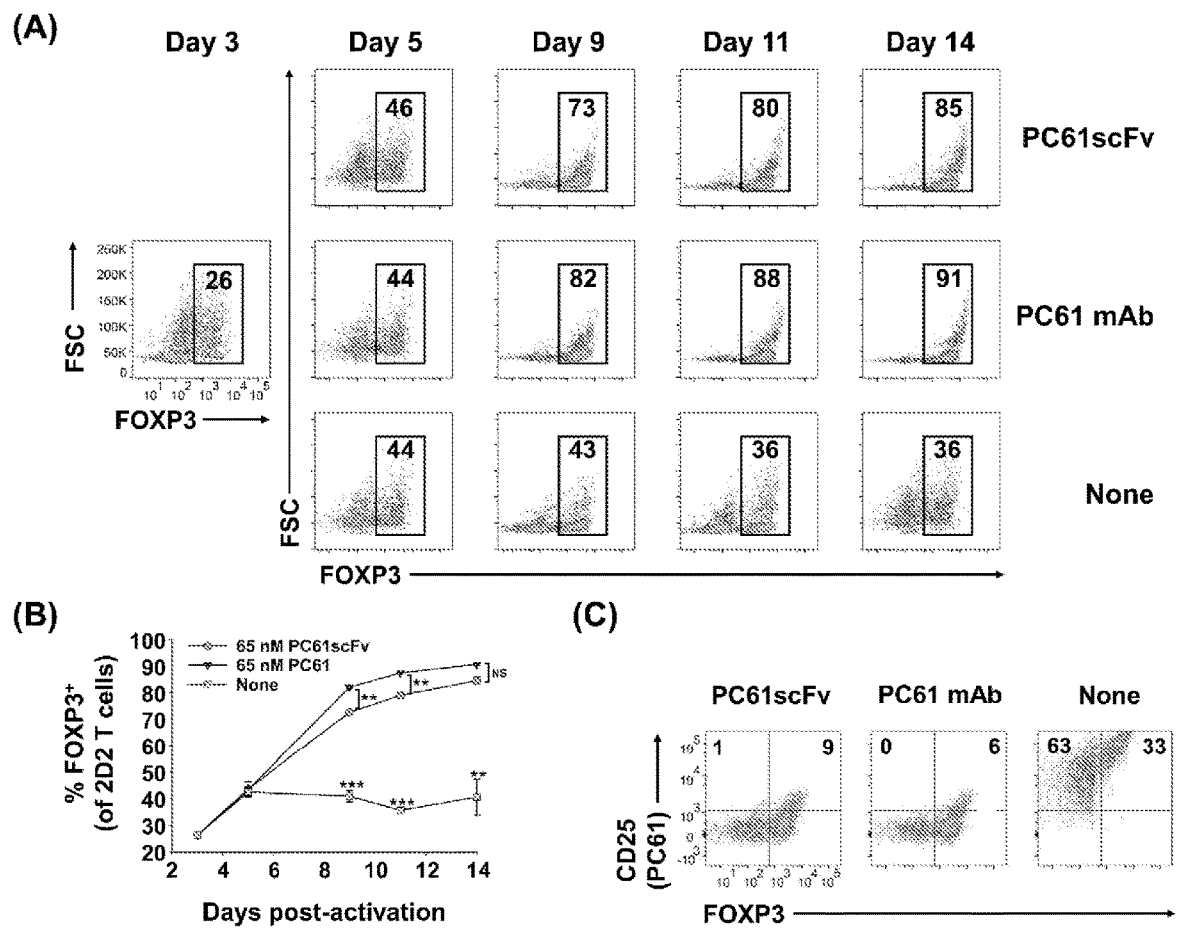

FIG. 11. Like the intact PC61 mAb, the monovalent PC61scFv stabilized Treg lines. 2D2-FIG SPL were activated at a density of $2 \times 10^6$ cells/ml in cRPMI with MOG35-55 (1 µM) in the presence of TGF-β (10 nM). After 3 days of activation, T cells were cultured (n=2) at a density of 500,000 cells/ml in IL-2 together with 65 nM PC61scFv, 65 nM PC61 mAb, or vehicle. Cells were passaged under the same conditions every 3-4 days. (panels A-B) Representative dotplots and timecourse data show FOXP3$^+$ Treg percentages in the Vβ11+ T cell population (values given at the top of each gate). *p<0.001, p<0.01, NS: not significant. (panel C) Vβ11$^+$ T cells were analyzed for expression of FOXP3 and the binding of an APC-conjugated PC61 mAb to surface CD25. These data are representative of three independent experiments.

DETAILED DESCRIPTION

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of +10%, +5%, +1%, ±0.5%, or even ±0.1% of the specified value as well as the specified value. For example, "about X" where X is the measurable value, is meant to include X as well as variations of ±10%, ±5%, ±1%, 0.5%, or even ±0.1% of X. A range provided herein for a measureable value may include any other range and/or individual value therein.

It will also be understood that, as used herein, the terms "example," "exemplary," and grammatical variations thereof are intended to refer to non-limiting examples and/or variant embodiments discussed herein, and are not intended to indicate preference for one or more embodiments discussed herein compared to one or more other embodiments.

The term "modulate," "modulates" or "modulation" refers to enhancement (e.g., an increase) or inhibition (e.g., a reduction) in the specified activity.

As used herein, the terms "increase," "increases," "increased," "increasing," "improve," "enhance," and similar terms indicate an elevation in the specified parameter and/or activity of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter and/or activity of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

The term "regulate" as used herein refers to the ability to affect a method, process, state of being, disorder or the like. The effect may be that of prevention, treatment or modulation.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom associated with a condition (e.g., an immunological and/or metabolic disorder) is achieved and/or there is a delay in the progression of the at least one clinical symptom. In some embodiments, the severity of a symptom associated with an immunological and/or metabolic disorder may be reduced in a subject compared to the severity of the symptom in the absence of a method of the present invention.

The terms "prevent," "preventing" and "prevention" (and grammatical variations thereof) refer to avoidance, reduction and/or delay of the onset of a symptom associated with a condition (e.g., an immunological and/or metabolic disorder) and/or a reduction in the severity of the onset of symptom associated with a condition (e.g., an immunological and/or metabolic disorder) relative to what would occur in the absence of a method of the present invention. The prevention can be complete, e.g., the total absence of the symptom. The prevention can also be partial, such that the occurrence of the symptom in the subject and/or the severity of onset is less than what would occur in the absence of a method of the present invention. Alternatively stated, the present methods may slow, delay, control, or decrease the likelihood or probability of the condition in the subject, as compared to that which would occur in the absence of the measure taken.

A "therapeutically effective" or "effective" amount is intended to designate a dose that causes a relief of symptoms of a condition (e.g., a disease or disorder) as noted through clinical testing and evaluation, patient observation, and/or the like. "Effective amount" or "effective" can further designate a dose that causes a detectable change in biological and/or chemical activity. The detectable changes may be detected and/or further quantified by one skilled in the art for the relevant mechanism or process. Moreover, "effective amount" or "effective" can designate an amount that maintains a desired physiological state, i.e., reduces or prevents significant decline and/or promotes improvement in the condition of interest. As is generally understood in the art, the dosage will vary depending on the administration routes, symptoms and body weight of the patient but also depending upon the compound being administered.

"Immune response" generally refers to innate and acquired immune responses including, but not limited to, both humoral immune responses (mediated by B lymphocytes) and cellular immune responses (mediated by T lymphocytes). An immune response may be beneficial and lead to immunity against infectious pathogens, or an immune response may be pathogenic and lead to autoimmune or hypersensitivity disease. Immune responses against foreign viruses, bacteria, fungi, parasites typically represent beneficial adaptive immune responses. Immune responses against self tissues, innocuous foreign objects (e.g., dust mite or pollen allergens, etc.), or tissue transplants represent examples of adverse maladaptive immune responses.

The term "antigen" as used herein means a substance or compound that stimulates an immune response. Although usually a protein or polysaccharide, antigens may be any type of molecule, which can include small molecules (haptens) that are coupled to a carrier-protein.

By the term "immunogenic" it is meant any substance or compound that stimulates an immune response.

By the term "tolerogen" it is meant any substance that stimulates immunological tolerance. By the terms "tolerogenic" or "tolerogenic activity" it is meant that a response of immunological tolerance is induced by an antigen or antigenic substance or an activity that results in the induction of immunological tolerance toward an antigen or antigenic substance. The term "tolerance" as used herein refers to a decreased level of an immune response, a delay in the onset or progression of an immune response and/or a reduced risk of the onset or progression of an immune response. "Specific" immunological tolerance occurs when immunological tolerance is preferentially invoked against certain antigens in comparison with others. "Active" immunological tolerance refers to a state in which the tolerance effect(s) are the result of an ongoing biological process: for example, down-regulation of specific effector cells by suppressor cells. "Sustained tolerance" is tolerance that measurably persists for an extended period of time.

The embodiments described herein may include, comprise, consist essentially of or consist of the Treg populations described herein.

Various populations of Tregs have been described and include natural thymic-derived $CD4^+$ $FOXP3^+$ Tregs and peripheral $CD4^+$ $FOXP3^+$ Tregs. These subsets, including both natural thymic Tregs and peripheral Tregs, can suppress immune responses, can play important roles in immunotherapy of autoimmune diseases, and can provide transplantation tolerance. These $FOXP3^+$ Treg subsets represent only about 5-10% of the $CD4^+$ T cells in the peripheral blood and are in a hypoproliferative state which has hampered detailed characterization and the potential use of these cells in a therapeutic setting. It has also been reported that only about 40-50% of $CD4^+$ $FOXP3^+$ Tregs T-cells are $CD25^{high}$ effector Tregs in peripheral blood. In vivo application therefore has relied on in vitro expansion protocols to generate sufficient numbers of $CD4^+$ $CD25^{high}$ $FOXP3^+$ Tregs for in vivo use. The clinical use of Tregs is limited by the lack of suitable maintenance and expansion protocols to generate sufficient numbers for in vivo infusion. Moreover, while activation of naïve T-cells in the presence of TGF-β can elicit an initial differentiation of Tregs, for example, $FOXP3^+$ Tregs, these Treg lines lack phenotypic stability and rapidly convert to a conventional T-cell (Tcons) phenotype during in vitro propagation in IL-2.

Accordingly, embodiments of the present invention provide methods of growing or expanding, propagating and/or maintaining a population of Tregs from a T-cell population. It will be understood by one of skill in the art that T-cells, i.e., thymus-derived cells that participate in a variety of cell-mediated immune reactions, may include Tregs, as well Tcons and non-regulatory T-cells (non-Tregs). The methods of the present invention are based in part on the discovery that the growth or propagation and maintenance of Tregs under suitable conditions can be directed and favored over the growth and propagation of Tcons and non-Tregs, and that these Tregs can be stably grown or expanded, propagated and/or maintained in vitro. Methods of the present invention allow for the generation of Tregs in sufficient numbers and purity for research purposes and for clinical use by infusion in patients. In some embodiments, a method and/or composition of the present invention may preserve the phenotype of a Treg population and/or one or more immunosuppressive activities of a Treg population. In some embodiments, FOXP3 Tregs maintain stability when propagated in a propagation culture (i.e., rest culture) with low concentrations of an anti-inflammatory cytokine, for example, IL-2, and high concentrations of an anti-inflammatory cytokine receptor inhibitor, for example, an anti-CD25 mAb (e.g., PC61).

It will be appreciated by one of skill in the art that sources of T-cells and methods of isolating particular T-cell populations (e.g., CD4$^+$ cells), which can be used to prepare a Treg population according to the present invention, are well known and described in the literature. For example, T-cells may be conveniently isolated from the blood, e.g., from a peripheral mononuclear cell (PMBC) population isolated from blood, or from other blood-derived preparations such as leukopheresis products or from bone marrow, lymph, thymus, spleen or umbilical cord. T-cells may be derived from any appropriate source, including human or animal sources. In some embodiments, T-cells may be obtained and/or derived from a subject (i.e., source T-cells) to be treated by a Treg population produced and/or derived from the source T-cells.

Thus, in some embodiments, a method of preparing a Treg population includes providing T-cells and exposing T-cells to a medium suitable for preferentially favoring growth and propagation of Tregs over Tcons, and growing, propagating and/or expanding Tregs from the T-cells to provide a Treg population, or an enriched Treg population, i.e., a T-cell population having a Treg population that percentagewise is higher than it was prior to exposure and/or propagation steps. In some embodiments, the Treg population provided based on a method of the present invention includes at least 35%, 40%, 45%, 50%, 55%, 60%, 65%, 70%, 75%, 80%, 85%, 90%, 91% 92%, 93%, 94%, 95%, 96%, 97%, 98% and/or 99% Tregs based on the total amount of T-cells present. Without a method of the present invention, Tregs cultured with IL-2 but without a stabilizing agent can provide Treg percentages typically less than 30%, 20%, 10%, 7%, 5%, 3%, or 1% of the total T-cell population.

In some embodiments, the conditions favoring the growth and propagation of Tregs rely on the differential blocking or inhibition of anti-inflammatory cytokine-dependent growth of Tcons and Tregs. Although not particularly limited, the blocking or inhibition of anti-inflammatory cytokine-dependent growth of Tcons may be accomplished by inhibiting the interaction between an anti-inflammatory cytokine and an anti-inflammatory cytokine receptor. This inhibition may be accomplished by, for example, an antibody to the anti-inflammatory cytokine receptor. In some embodiments, the interaction blocked or inhibited is an interaction of IL-2 with an IL-2 receptor.

In some embodiments, the differential inhibition of anti-inflammatory cytokine-dependent growth of Tcons and Tregs may rely on the differential expression of an anti-inflammatory cytokine receptor between Tcons and Tregs, for example, an anti-inflammatory cytokine receptor that is expressed constitutively at high levels in Tregs, but is expressed only transiently at high levels in Tcons. The constitutive expression of IL-2 receptor alpha (CD25) is considered to be a characteristic feature of Tregs. Thus, in some embodiments, IL-2-dependent growth of Tcons is blocked or inhibited by inhibiting the interaction of IL-2 with CD25. Although not necessarily limited thereto, in some embodiments, an inhibitor of the interaction between an anti-inflammatory cytokine and an anti-inflammatory cytokine receptor may be an antibody and/or a fragment thereof (e.g., a single chain FV antibody). In some embodiments, the antibody and/or fragment thereof may be a monoclonal antibody and/or fragment thereof. For example, the antibody and/or fragment thereof may be an anti-CD25 antibody and/or a fragment thereof. The particular antibody is not necessarily limited. Exemplary antibodies include IgA, IgD, IgE, IgG and IgM, and their various subclasses, for example, IgA1, IgA2, IgG1, IgG2, IgG3 and IgG4, and/or fragments thereof. The antibody and/or fragment thereof may have a kappa (κ) light chain or a lambda (λ) light chain, and may be from any organism, human or non-human. In some embodiments, the antibody and/or fragment thereof can be PC61, a rat IgG1, k monoclonal antibody to CD25. In some embodiments, the antibody and/or fragment thereof can be 7D4, a rat IgM, K monoclonal antibody. In some embodiments, the Treg stabilizing entity may be an antibody, (e.g., a monoclonal antibody) or a fragment thereof, or a recombinant protein that binds, inhibits, regulates, and/or modifies the activity of human CD25 or a component of the IL-2 receptor signaling complex, including IL-2 receptor-beta (CD122) and/or IL-2 receptor-gamma (CD132) or other downstream signaling pathways to provide preferential growth of human Tregs in mixed cultures of Tregs and non-Treg conventional T cells. In some embodiments, the antibody may have a specificity similar to or overlapping with that of an anti-human CD25 antibody such as, e.g., Daclizumab, Basiliximab, 7G7B6, 2A3, M-A251, BC96, and/or other reagents that modify the activity of the human IL-2 signaling complex. In some embodiments, the inhibitor of the interaction between an anti-inflammatory cytokine and an anti-inflammatory cytokine receptor may be a single chain Fv (scFv) fragment (see, e.g., FIG. 11). The antibody and/or fragment thereof may directly or indirectly inhibit the binding the anti-inflammatory cytokine to its receptor, for example, the binding of IL-2 to CD25. The antibody and/or fragment thereof may keep IL-2 signaling in the low-zone intensity range.

In some embodiments, an anti-human CD25 monoclonal antibody or fragment thereof (e.g., an anti-human CD25 single-chain Fv (scFv) recombinant protein) has an amino acid sequence that is at least 70% (e.g., at least 70%, 75%, 80%, 85%, 90%, 95%, 97%, 98%, 99%, or more) identical to the amino acid sequence for PC61 or a fragment thereof such as, e.g., an amino acid sequence including the variable heavy domain (e.g., SEQ ID NO:6) and the variable light domain (e.g., SEQ ID NO:7) of PC61 (e.g., as described in Huss D J, et al. Immunology (2016) 148(3):276-86. Epub 2016/03/26. doi: 10.1111/imm.12609. PubMed PMID: 27012310; PubMed Central PMCID: PMCPMC4913290). An anti-human CD25 monoclonal antibody or fragment thereof may induce and/or stabilize Tregs as described herein. In some embodiments, an anti-human CD25 monoclonal antibody or fragment thereof may provide the same or substantially the same (e.g., ±20% or less) degree of Treg stability as provided by PC61. For example, the anti-human CD25 monoclonal antibody or fragment thereof may provide an amount of Tregs based on the total amount of T-cells present in a culture that this the same or substantially the same (e.g., +20% or less) as the amount provided by PC61.

In some embodiments, a method of preparing a Treg population may include activation of T-cells, for example, activation of naïve T-cells in the presence of TGF-β and/or IFN-β, to provide an initial differentiation of T-cells to provide a lineage of Tregs in the T-cell population. In some embodiments, the activated T-cells, including a lineage of Tregs, can be CD4$^+$ T-cells. In some embodiments, the lineage of Tregs includes FOXP3$^+$ Tregs that may constitutively express CD25. Thus, in some embodiments, the lineage of Tregs includes CD4$^+$CD25$^+$FOXP3$^+$ Tregs.

Activation of T-cells may also take place in the presence of an antigen. In some embodiments, the antigen may be a peptide such as, e.g., a synthetic peptide. Activation of T-cells in the presence of an antigen can provide a lineage of antigen-specific Tregs. In some embodiments, the antigen can be MOG35-55. In some embodiments, a mitogen such as, e.g., Con-A, or a superantigen such as, e.g., *Staphylococcus aureus* enterotoxin (SEB), provides the activating signal in the presence or absence of a specific antigen. The activation of T-cells may take place in the presence of an anti-inflammatory cytokine receptor inhibitor, such as, e.g., an antibody to an anti-inflammatory cytokine receptor (e.g., an anti-CD25 monoclonal antibody), or the activation of T-cells may take place in the absence of an anti-inflammatory cytokine receptor inhibitor, prior to exposing and propagating T-cells in the presence of an anti-inflammatory cytokine and the anti-inflammatory cytokine receptor inhibitor. In some embodiments, activation of T-cells takes place in the absence of the anti-inflammatory cytokine receptor inhibitor.

In some embodiments, a Treg population may be maintained in vitro via an activation-rest cycle whereby an approximate 3-4 day activation culture is followed by a series of about 3-4 day propagation cultures over the course of about 1-3 weeks. This cycle can then be repeated such as, e.g., 2, 3, 4, 5, 6, 7, 8, 9, 10 or more times or indefinitely. An activation culture of the present invention may include a stimulus (e.g., an antigen, mitogen, and/or superantigen) and antigen presenting cells (e.g., dendritic cells, macrophages, etc). To maintain Treg stability during activation, the culture may include TGF-β and/or IFN-β, e.g., with 100 pM, 1 nM, 10 nM, or higher concentrations of TGF-β and/or with 1 nM, 10 nM, 100 nM, or 1 µM, or higher concentrations of IFN-β. In some embodiments, TGF-β may be present in a culture of the present invention at a concentration in a range of about 1 pM to about 10 nM and/or IFN-β may be present in a culture of the present invention at a concentration in a range of about 1 nM to about 10 µM. In some embodiments, the culture includes IFN-β and not TGF-β to maintain Treg stability during activation. In some embodiments, the activation culture may comprise an anti-inflammatory cytokine (e.g., IL-2). If the activation culture includes IL-2, then an anti-CD25 reagent may be present in the activation culture to limit IL-2 signaling.

While not wishing to be bound to any one particular theory, conditions under which anti-inflammatory cytokine-mediated growth of T-cells are favorable for Tregs can be described as being part of or within a "Treg window." Differential IL-2 responsiveness distinguishes Tregs, for example, FOXP3$^+$ Tregs from conventional T-cell subsets. As such, the relative concentrations of an anti-inflammatory cytokine and an anti-inflammatory cytokine receptor inhibitor may be adjusted to favor dominant survival and expansion of Tregs and to achieve long-term stable growth of Tregs. Thus, in some embodiments, such conditions may include the presence of an anti-inflammatory cytokine, for example, IL-2, and an anti-inflammatory cytokine receptor inhibitor, for example, an anti-CD25 antibody, at concentrations in which the anti-inflammatory cytokine-mediated T-cell growth, propagation and/or expansion of Tcons and/or non-Tregs is substantially or completely blocked or inhibited, whereas growth, propagation and/or expansion of Tregs is only partially blocked, thus favoring growth of Tregs from the T-cell population.

The conditions that are part of or within a "Treg window" may be noted by low concentrations of the anti-inflammatory cytokine in conjunction with high concentrations of the anti-inflammatory cytokine receptor inhibitor. If the concentration of anti-inflammatory cytokine is too high, for example, concentrations of IL-2 greater than about 10 nM, inhibitory actions of the anti-inflammatory cytokine receptor inhibitor on anti-inflammatory cytokine-dependent T-cell growth, propagation and/or proliferation of Tregs may be overwhelmed and conventional T cell subsets may instead dominate the culture. Thus, in some embodiments, the concentration of an anti-inflammatory cytokine, for example, IL-2, may be in a range of about 1 pM to about 100 pM, about 100 pM to about 10 nM, about 100 pM to about 3.2 nM, about 100 pM to about 320 pM, about 320 pM to about 10 nM, or about 320 pM to about 3.2 nM. The concentration of an anti-inflammatory cytokine receptor inhibitor, for example, an anti-CD25 antibody such as, e.g., PC61, may be up to about 1 µM, up to about 100 nM or up to about 10 nM.

The Treg population grown and provided under the conditions of the present invention can also be stably maintained over a period of time. Following activation of T-cells to provide Tregs, such as FOXP3$^+$ Tregs, T-cell populations passaged over a period of time in the presence of an anti-inflammatory cytokine, such as IL-2, will exhibit a decrease in the percentage of Tregs in the T-cell population during subsequent propagation. Thus, in some embodiments of the invention, exposing and growing the T-cells in the presence of an anti-inflammatory cytokine, such as, e.g., IL-2, and in the presence of an anti-inflammatory cytokine receptor inhibitor, such as a human anti-CD25 antibody under the conditions such as those set forth herein, can result in preferential outgrowth of Tregs, resulting in a T-cell population having at least 35%, 40%, 45%, 50%, 55%, 60%, 65%, 70%, 75%, 80%, 85%, 90%, 91% 92%, 93%, 94%, 95%, 96%, 97%, 98% and/or 99% Tregs based on the total amount of T-cells present.

In some embodiments, T-cells, such as, activated T-cells, may be exposed to or passaged into a medium including an anti-inflammatory cytokine, such as IL-2 and an inhibitor, such as, e.g., an antibody to an anti-inflammatory cytokine receptor, for example, an anti-human CD25 monoclonal antibody with an epitope specificity parallel to that of the anti-murine CD25 monoclonal antibody PC61. The concentrations of the anti-inflammatory cytokine receptor inhibitor for growing and propagating the T-cells that result in an enrichment of Tregs to provide a Treg population, will be dependent upon the inhibitor. For example, concentrations of an anti-inflammatory cytokine receptor (e.g., anti-CD25) in the medium may be about 1 µg/ml to about 32 µg/ml. In some embodiments, the concentration of an anti-inflammatory cytokine receptor (e.g., anti-CD25) may be about 1 µg/ml, about 10 µg/ml or about 32 µg/ml. The concentration of anti-inflammatory cytokine, such as IL-2, in the medium, may be about 0.1% to about 1.0% (v/v) or about 1 unit/ml to about 10, 20, 30, 40, 50, 60, 70, 80, 90, or 100 units per ml. In some embodiments, the concentration of the anti-inflammatory cytokine may be about 0.1% or about 1.0% (v/v). It should be noted that in some embodiments, these concentrations are presented as a dilution (v/v) of an expression media from a recombinant baculovirus/Sf9 insect cell culture that is being used as an abundant source of IL-2.

Thus, according to some embodiments of the invention, a Treg population can be grown or propagated from activated T-cells in media comprising low concentrations of an anti-inflammatory cytokine, such as IL-2, and high concentrations of an anti-inflammatory cytokine receptor inhibitor, such as, e.g., monoclonal anti-CD25 antibody with an epitope specificity parallel to that of the PC61 antibody as set forth hereinabove, without additional physical purification. The growth or propagation and maintenance of the Treg population, for example a T-cell population comprising 90% or more Tregs, under these conditions may be indefinite, or for example, at least about 2, 3, 4, 5, 6, 7, 8, 9, 10, 11, 12, 13, 14, 15, 16, 17, 18, 19, 20, 21, 22, 23, 24, 25, 26 or more days, weeks, or months or, for example, at least about any number of days between 14-105 days, for example, 14 days, 15 days, 20 days, 25 days, 30 days, 35 days, 40 days, 45 days, 50 days, 55 days, 60 days, 65 days or 68 days, 70 days, 75 days, 80 days, 85 days, 90 days, 95 days, 100 days, 105 days or more. In some embodiments, the phenotype of the Treg population and/or one or more immunosuppressive activities of the Treg population may be preserved during the growth or propagation and maintenance of the Treg population (e.g., indefinitely, or 2, 6, 8, 10, 12, 14, 16, 18, 20 22, 24, 26 or more days, weeks, or months).

According to some embodiments of the present invention, a method of the present invention may comprise co-culturing T-cells (e.g., $CD4^+$ $CD45RA^+$ purified naïve T-cells) with antigen presenting cells (e.g., dendritic cells, macrophages, etc.) in the presence of a stimulus (e.g., an antigen, mitogen, and/or superantigen) for about 2-8 or 3-7 days (e.g., about 2, 3, 4, 5, 6, 7, 8 days) to induce and expand a Treg population. In some embodiments, $CD4^+$ $CD45RA^+$ purified naïve T-cells may be co-cultured with autologous immature monocyte-derived dendritic cells in the presence of an antigen and TGF-β and/or IFN-β, optionally with other supplements such as, e.g., Vitamin C, for about 3-7 days to induce and expand antigen-specific $FOXP3^+$ $CD25^+$ Tregs. Then, the T-cells may be rested in media containing an anti-inflammatory cytokine (e.g., IL-2) and an anti-inflammatory cytokine receptor inhibitor (e.g., an anti-CD25 monoclonal antibody, scFv, or other agent that limits IL-2 signaling) to generate high percentages of antigen-specific Tregs ("resting step"). These antigen-specific Tregs may be propagated every about 3 or 4 days for about 1-2 weeks or more in media containing an anti-inflammatory cytokine (e.g., IL-2) and an anti-inflammatory cytokine receptor inhibitor (e.g., anti-CD25 agent) ("propagation step"). The Tregs may then be re-activated by co-culturing with antigen presenting cells (e.g., autologous monocyte-derived DCs), stimulus (e.g., antigen), and TGF-β and/or IFN-β, optionally with growth supplements (e.g., Vitamin C), in the presence of an anti-inflammatory cytokine (e.g., IL-2) and an anti-inflammatory cytokine receptor inhibitor (e.g., anti-CD25 agent) for about 3-4 days ("re-activation step"). The resting, propagation, and re-activation steps may be repeated 1 or more times (e.g., 2, 3, 4, or more times), which may generate high numbers of pure, antigen-specific Tregs (e.g., high numbers of pure, antigen-specific $FOXP3^+$ $CD25^+$ Tregs) that may be suitable for adoptive immunotherapy Embodiments of the present invention provide methods of treating or modulating an immunological and/or metabolic disorder including administering to a subject an effective amount of a Treg population, a composition comprising a Treg population, and/or a pharmaceutical formulation comprising a Treg population prepared as set forth herein. A composition and/or formulation of the present invention may be "pharmaceutically acceptable". "Pharmaceutically acceptable" as used herein means that the composition and/or formulation is suitable for administration to a subject without unduly deleterious side effects in light of the severity of the condition and necessity of the treatment.

In some embodiments, a composition and/or method of the present invention may be used in an adoptive immunotherapy method and/or treatment. For example, a Treg population, formulation, and/or composition of the present invention may be infused into a patient.

According to embodiments of the present invention, exemplary immunological disorders include, but are not limited to, autoimmune diseases, allergic or hypersensitivity diseases, transplant rejection, chronic inflammatory and/or tissue disorders.

Autoimmune diseases include, but are not limited to, those affecting the following organ systems. Nervous system: Acute disseminated encephalomyelitis (demyelinating inflammation following vaccination or infection); Myasthenia Gravis (anti-AchR antibodies, blockade of neuromuscular junction); Multiple sclerosis (inflammation of CNS myelin); Acute inflammatory demyelinating polyneuropathy/Guillain-Barre syndrome (inflammation of peripheral myelin); Endocrine system: Hashimoto's Thyroiditis (anti-thyroid antibodies, hypothyroidism); Grave's Disease (autoantibodies stimulate TSH receptors on thyroid follicular cells, hyperthyroidism); Insulin-Dependent Diabetes Mellitus (i.e. juvenile diabetes, inflammation and deletion of (3 islet cells); Autoimmune adrenal insufficiency (e.g. Addison's disease, inflammation coupled with progressive scarring and atrophy of adrenal glands); Autoimmune oophoritis (inflammation of ovaries, infertility); Autoimmune orchitis. (inflammation of testis); Hematopoietic system: Autoimmune hemolytic anemia (anti-erythrocyte antibodies); Paroxysmal cold hemoglobinuria (mediated by IgM cold agglutinins against erythrocytes); Idiopathic thrombocytopenic purpura (anti-platelet antibodies, bleeding); Autoimmune neutropenia (antibodies against neutrophils cause degranulation, neutrophil depletion, and vasculitis); Pernicious anemia (progressive destruction of gastric fundic gland, loss of intrinsic factor, and malabsorption of vitamin $B_{12}$); Autoimmune coagulopathy (circulating anti-coagulants, anti-phospholipid antibody syndrome, neutralizes phospholipids necessary for clotting activity); Gastrointestinal Tract: Primary biliary cirrhosis (intrahepatic bile duct and portal inflammation leading to fibrosis and cirrhosis); Inflammatory bowel disease (Crohn's disease, ulcerative colitis); Kidney: Glomerulonephritis (antibody against glomerular basement membrane); Immune complex glomerular nephritis (accumulation of deposited immune complexes in basement membrane); Skin: Pemphigus vulgaris (loss of adhesion between epidermal cells, blistering, antibody against stratified squamous epithelium); Systemic autoimmune disease: Systemic Lupus Erythematosus (arthralgias, rash, nephritis, anti-nuclear antibodies); Rheumatoid Arthritis (inflammatory polyarticular arthritis, rheumatoid factor); Sjogren's syndrome (inflammation of lacrymal and parotid glands with arthritis); Polymyositis (inflammation of skeletal muscle); Dermatomyositis (inflammation of skin and skeletal muscle); Scleroderma (progressive systemic sclerosis, sclerosis of skin and internal organs); and Cardiac and vascular diseases: Autoimmune myocarditis (inflammation of cardiac muscle); Immune complex-mediated vasculitis (passive deposition of immune complexes in vessel walls followed by C-mediated lysis and inflammation); Polyarteritis *nodosa* (type of necrotizing vasculitis that follows certain types of infections). In some embodiments of the present invention, the autoimmune disease is an autoimmune disease affecting the nervous system, endocrine system, hematopoietic system, gastrointestinal tract, renal system, cardiac system, vascular system, musculoskeletal system or a combination thereof. In some embodiments, the autoimmune disease is a systemic autoimmune disease. In some embodiments, the autoimmune disease is multiple sclerosis.

Allergic or hypersensitivity diseases include, but are not limited to, allergic rhinitis, asthma, atopic dermatitis, allergic gastroenteropathy, contact dermatitis, drug allergy or a combination thereof. In some embodiments, the present invention provides active agents, compositions and methods to induce antigen-specific immunological tolerance to allergens responsible for the allergic diseases described herein.

Transplant rejection and tissue disorders include, but are not limited to, those affecting the kidney, liver, pancreas, heart, lung, bone, skin and combinations thereof. In some embodiments, the present invention provides compositions and methods to induce antigen-specific immunological tolerance to allogeneic and/or xenogeneic transplantation antigens that may contribute to the rejection of tissue transplants, and thus, facilitate acceptance of kidney transplants, liver transplants, pancreas transplants, skin grafts, heart transplants, and heart-lung transplant. The active agents and methods may also alleviate complications of bone marrow transplantation (i.e., graft versus host disease).

Exemplary metabolic disorders include, but are not limited to metabolic syndrome, diabetes (e.g., Type 1 diabetes and type II diabetes), obesity, cardiovascular disease including arteriosclerosis and atherosclerosis, and other inflammation-associated disorders associated with dysregulation of the body's energy storage systems and/or metabolism.

It is contemplated that diseases and/or disorders treated by the methods of this invention can include any disease or disorder that can be treated by mounting an effective tolerogenic response by the Treg population or any disease that can be treated by a composition comprising a Treg population and/or a pharmaceutical formulation comprising a Treg population prepared as set forth herein. Accordingly, embodiments of the present invention provide methods of modulating an immune response in a subject including administering a Treg population to the subject in an amount sufficient to elicit a tolerogenic response. In some embodiments, the immune response is antigen-specific. In some embodiments, the administering step is carried out in vivo or ex vivo. In some embodiments, the tolerogenic response is an active tolerance mechanism. In some embodiments, the tolerogenic response is a sustained tolerogenic response.

It is also contemplated that the Treg population, compositions comprising the Treg population, and/or pharmaceutical formulations comprising the Treg population of this invention can be used as a vaccine and/or prophylactic composition and employed in methods of preventing a disease or disorder in a subject, comprising administering to the subject an effective amount of the active agent (e.g., a Treg population) of this invention. The vaccine can be administered to a subject who is identified to be at risk of contracting a particular disease or developing a particular disorder and in whom the ability to elicit an immune response to an antigen may be impaired. Identification of a subject at risk can include, for example, evaluation of such factors as family history, genetic predisposition, age, environmental exposure, occupation, lifestyle and the like, as are well known in the art.

Having now described the invention, the same will be illustrated with reference to certain examples, which are included herein for illustration purposes only, and which are not intended to be limiting of the invention.

EXAMPLES

Example 1

FOXP3$^+$ regulatory T cells (Tregs) represent a promising platform for effective adoptive immunotherapy of chronic inflammatory disease, including autoimmune diseases such as Multiple Sclerosis. Successful Treg immunotherapy however requires new technologies to enable long-term expansion of stable, antigen-specific FOXP3$^+$ Tregs in cell culture. Antigen-specific activation of naïve T cells in the presence of TGF-β elicits the initial differentiation of the FOXP3$^+$ lineage, but these Treg lines lack phenotypic stability and rapidly transition to a conventional T cell (Tcon) phenotype during in vitro propagation. Because Tregs and Tcons differentially express CD25, we hypothesized that anti-CD25 monoclonal antibodies (mAbs) would only partially block IL-2 signaling in CD25$^{high}$ FOXP3$^+$ Tregs while completely blocking IL-2 responses of CD25$^{low-intermediate}$ Tcons to enable preferential outgrowth of Tregs during in vitro propagation. Indeed, murine TGF-(3-induced MOG-specific Treg lines from 2D2 transgenic mice that were maintained in IL-2 with the anti-CD25 PC61 mAb rapidly acquired and indefinitely maintained a FOXP3$^{high}$ phenotype during long-term in vitro propagation (>90% FOXP3$^+$ Tregs) whereas parallel cultures lacking PC61 rapidly lost FOXP3. These results pertained to TGF-β-inducible 'iTregs' because Tregs from 2D2-FIG Rag1$^{-/-}$ mice, which lack thymic or natural Tregs, were stabilized by continuous culture in IL-2 and PC61. MOG-specific and polyclonal Tregs up-regulated the Treg-associated markers Neuropilin-1 (NRP1) and Helios (IKZF2). Just as PC61 stabilized FOXP3$^+$ Tregs during expansion in IL-2, TGF-β fully stabilized FOXP3$^+$ Tregs during cellular activation in the presence of dendritic cells and antigen/mitogen. Adoptive transfer of blastogenic CD25$^{high}$ FOXP3$^+$ Tregs from MOG35-55-specific 2D2 TCR transgenic mice suppressed experimental autoimmune encephalomyelitis (EAE) in pretreatment and therapeutic protocols. In conclusion, low IL-2 concentrations coupled with high PC61 concentrations constrained IL-2 signaling to a low-intensity range that enabled dominant stable outgrowth of suppressive CD25$^{high}$ FOXP3$^+$ Tregs. The ability to indefinitely expand stable Treg lines will provide insight into FOXP3$^+$ Treg physiology and will be foundational for Treg-based immunotherapy.

Materials and Methods:

Mice.

C57BL/6 mice, MOG35-55 specific TCR transgenic 2D2 mice (B6-Tg(Tcra2D2,Tcrb2D2)1Kuch/J) (Stock Number 006912), OVA323-339 specific TCR transgenic OT-II mice (Stock Number 004194), B6.129S7-Rag1$^{tm1Mom}$/J (Stock Number 002216), and Foxp3-IRES-GFP knock-in (FIG) mice (B6.Cg-Foxp3$^{tm2Tch}$/J, Stock Number 006772) were obtained from Jackson Laboratory (Bar Harbor, Me.) and were maintained as a colony in the Department of Comparative Medicine. In the 2D2-FIG and OTII-FIG strains, the FIG GFP reporter was used as a surrogate marker of FOXP3 expression. Routine screening of 2D2 mice was performed by FACS analysis of PBMC by use of antibodies specific for TCR Vβ11 and/or Vα3.2. Routine screening of OT-II mice was performed by FACS analysis of PBMC by use of antibodies specific for TCR Vβ5.1/5.2 and Vα2. The FIG genotype was screened by use of forward (SEQ ID NO:1; CAC CTA TGC CAC CCT TAT CC) and reverse (SEQ ID NO:2; ATT GTG GGT CAA GGG GAA G) primers. Animal care and use was performed in accordance with approved animal use protocols and guidelines of the East Carolina University Institutional Animal Care and Use Committee.

MOG35-55, OVA323-339, TGF-β, and IL-2.

Synthetic MOG35-55 (SEQ ID NO:3; MEVGWYRSPFSRVVHLYRNGK) and OVA323-339 (SEQ ID NO:4; ISQAVHAAHAEINEAGR) peptides were obtained from Genscript (Piscataway, N.J.). Recombinant rat TGFβ1 was expressed by use of transfected human embryonic kidney (HEK) cells. TGFβ1 was expressed as described (Zou Z, Sun P D. *Protein Expr Purif* (2004) 37(2):265-72. doi: 10.1016/j.pep.2003.06.001. PubMed PMID: 15358346; and Wang D, et al. *J Immunol* (2016) 197:2992-3007. Epub 2016/09/14. doi: 10.4049/jimmunol.1500411. PubMed PMID: 27619998). This expression vector encoded a rat serum albumin leader sequence, an 8-histidine purification tag, the latency-associated peptide (LAP), the native RHRR cleavage site, and the C-terminal TGF-β1 sequence. A C32S substitution in the LAP domain enabled high level expression. The protein was expressed in HEK supernatants, purified on Ni-NTA affinity columns, and was activated by 10 minutes of exposure to 70° C. The bioactivity of each TGF-β1 preparation was verified by induction of FOXP3 in cultures of MOG-stimulated 2D2-FIG splenocytes (SPL). Recombinant rat IL-2 (~10-30 Units/ml) was derived from a baculovirus expression system and was used routinely in bulk T cell culture (Mannie M D, et al. *Immunol Cell Biol* (2003) 81(1):8-19. Epub 2003/01/22. doi: 10.1046/j.1440-1711.2003.01131.x. PubMed PMID: 12534941). Recombinant murine IL-2 was purified from a stable transfected HEK293F cell line.

Generation, Purification, and Administration of mAbs and PC61scFv.

The PC61-5.3 anti-CD25 rat IgG1(λ) hybridoma (Setiady Y Y, et al. *Eur J Immunol* (2010) 40(3):780-6. doi: 10.1002/eji.200939613. PubMed PMID: 20039297), the 7D4 anti-CD25 rat IgM(κ) hybridoma, and the 1D11.16.8 anti-mouse-TGF-β1/2/3 mouse IgG1 hybridoma (Dasch J R, et al. *J Immunol* (1989) 142(5):1536-41. PubMed PMID: 2537357; and Liu V C, et al. *J Immunol* (2007) 178(5):2883-92. PubMed PMID: 17312132) were obtained from ATCC. The 3C7 anti-CD25 rat IgG2b(κ) hybridoma was a generous gift from Dr. Ethan Shevach (NIH). All hybridomas were subcloned twice to ensure stability. Hybridoma supernatants were clarified at 7,200×g, precipitated with 50% ammonium sulfate, and dissolved in PBS. MAbs were purified on protein G agarose columns, eluted with 200 mM glycine at pH 3.0, and neutralized by 1M Tris buffer of pH 9.0. The purity of these mAb was verified by SDS-PAGE. Specific activities of PC61 preparations were measured by staining of murine $CD25^+$ T cells with serial ½ log dilutions of the mAb. After washing, PC61-stained T cells were labeled with a PE-conjugated goat anti-rat IgG(H+L) secondary antibodies followed by flow cytometric analysis.

The PC61scFv gene encoded (from N-terminus to C-terminus) the rat serum albumin signal peptide, a polyhistidine affinity purification tag, the PC61 variable light chain domain, a $(Glycine_4Serine_1)_4$ linker, and the PC61 variable heavy chain domain. The PC61 VL and VH domain sequences were described previously (Huss D J, et al. Immunology (2016) 148(3):276-86. Epub 2016/03/26. doi: 10.1111/imm.12609. PubMed PMID: 27012310; PubMed Central PMCID: PMCPMC4913290). The sequence was as follows: M-A-K-W-V-T-F-L-L-L-L-F-I-S-G-S-A-F-S-H-H-H-H-H-H-H-H-(Variable light chain domain)-G-G-G-G-S-G-G-G-G-S-G-G-G-G-S-G-G-G-G-S-(Variable heavy chain domain)-A-K-G-G-G-S-E-G-G-G-S-E-G-G-G-S-G (SEQ ID NO:5). The PC61scFv gene sequence was cloned into the pIRES AcGFP1 expression vector (Clontech) and used to stably transfect HEK293F cells. PC61scFv was purified using a column loaded with Ni-NTA resin, and purity was measured using SDS-PAGE. PC61scFv specificity and activity was validated by inhibition of IL-2-dependent proliferation of an IL-2-dependent cell line.

Flow Cytometric Analyses of SPL and PBMC.

Cells were washed in HBSS with 2% heat-inactivated FBS and stained for 1 hr at 4° C. in the dark with designated cocktails of fluorochrome-conjugated antibodies, including those specific for Vβ11 (KT11), Vβ5.1 (MR9-4), CD25 (PC61), CD25 (3C7), LAP (TW7-16B4), GARP (F011-5), GITR (DTA-1), PD-1 (29F-1A12), Nrp1 (3E12), Helios (22F6), CD69 (H1.2F3), ICOS (C398.4A), CTLA4 (UC10-4B9), TIGIT (1G9), CD44 (IM7), CD62L (MEL-14), CD45.1 (A20), and goat anti-rat IgG. Cells were then washed 3 times with HBSS/2% FBS. Data were collected by use of a Becton-Dickinson LSRII flow cytometer (San Jose, Calif.) and analyzed by use of FlowJo software.

Generation and Maintenance of Treg Lines.

Naïve SPL were harvested from 2D2-FIG mice, 2D2-FIG-Rag1$^{-/-}$ mice, OTII-FIG mice, or FIG mice. These SPL were activated at a density of 2×10$^6$/ml in complete RPMI (cRPMI; 10% heat-inactivated fetal bovine serum, 2 mM glutamine, 100 µg/ml streptomycin, 100 U/ml penicillin, 50 µM 2-ME) for 3-4 days with 1 µM MOG35-55, 100 nM OVA323-339, or 2.5 µg/ml Con-A, as indicated. Naïve FOXP3$^{null}$ T cells were isolated from 2D2-FIG SPL by FACS to support the in vitro generation of TGF-β-induced iTregs and thereby exclude the contribution of thymic/natural tTregs/nTregs in designated experiments. After the initial activation, T cells were passaged every 3-4 days in rat IL-2 and were periodically reactivated every 2-4 weeks by reactivation with specific antigen or mitogen in a 3-4 day culture with irradiated splenic APC to drive cellular activation and expand T cell numbers. The initial activation also included 10 nM TGF-β to elicit Treg differentiation, but TGF-β was not added during the subsequent maintenance passages of the line in rat IL-2. PC61 or a designated anti-CD25 antibody (10 µg/ml; 65 nM) was included in the activation and/or maintenance cultures as designated. Cells were propagated every 3-4 days in maintenance cultures containing cRPMI and rat IL-2 along with 10 µg/ml PC61 (or designated anti-CD25 antibody). For polyclonal Treg lines derived from FIG mice, CD4$^+$ cells were purified 10 days post-activation using magnetic bead positive selection (Miltenyi Biotec). Unless otherwise noted, subsequent reactivation of Tregs consisted of co-culturing irradiated SPL (2×10$^6$/ml) and 2D2-FIG Tregs (2×10$^5$/ml) in the presence of 1 µM MOG35-55, TGF-β (as designated), and rat IL-2 with or without PC61 as designated. After 3 days, activated Tregs were passaged into cRPMI containing rat IL-2 and 10 µg/ml PC61.

In Vitro Suppression Assay.

CD45.2 2D2-FIG Tregs were cultured in PC61 and IL-2 for either 13 days or 40 days, and a control line of CD45.2 2D2-FIG Tcons were cultured in IL-2 for 13 days. These Treg and control lines were used to test the ability of Tregs to suppress naïve 2D2-FIG T cell activation. CTV-stained CD45.1 2D2-FIG SPL (150,000/well) were used as responders. CTV-labeled responders were cultured with CD45.2 2D2-FIG Tregs or with CD45.2 2D2-FIG Tcons (25,000/well) in the presence or absence of 1 µM MOG35-55 and rat IL-2. After 5 days of culture, proliferation of CD45.1 2D2 T cells was analyzed by measuring CTV dilution.

Induction and Assessment of EAE.

CFA (Incomplete Freund's Adjuvant plus 4 mg/ml heat-killed *Mycobacterium tuberculosis* H37Ra, BD Biosciences, Franklin Lakes, N.J.) was mixed 1:1 with MOG35-55 in phosphate-buffered saline. The CFA/antigen mixture was emulsified by sonication. EAE was elicited in B6 mice by injection of 100 µg or 200 µg MOG35-55 in a total volume of 100 µl emulsion via three subcutaneous injections of 33

µl across the upper back. Each mouse received separate injections (200 nanograms i.p.) of Pertussis toxin on days 0 and 2. All immunizations were performed under isoflurane anesthesia (Abbott Laboratories, Chicago, Ill.). Mice were assessed daily for clinical score and body weight. The following scale was used to score the clinical signs of EAE: 0, no disease; 0.5, partial paralysis of tail without ataxia; 1.0, flaccid paralysis of tail or ataxia but not both; 2.0, flaccid paralysis of tail with ataxia or impaired righting reflex; 3.0, partial hind limb paralysis marked by inability to walk upright but with ambulatory rhythm in both legs; 3.5, same as above but with full paralysis of one leg; 4.0, full hindlimb paralysis; 5.0, total hindlimb paralysis with forelimb involvement or moribund. A score of 5.0 was a humane endpoint for euthanasia.

The incidence of EAE reflected the number of mice afflicted with EAE compared to the total group size. Cumulative EAE scores were calculated by summing daily scores for each mouse across the time course of disease. Maximal scores were calculated as the most severe EAE score for each mouse. Mice that did not exhibit EAE had a score of zero for the cumulative and maximal scores, and these scores were included in the group average. Mice that exhibited humane endpoints as assessed by body weight loss, body score, or clinical score of 5.0 were subjected to humane euthanasia and were omitted from scoring thereafter. Time-course graphs portrayed daily mean maximal scores. To calculate percent maximal weight loss, 100% body weight was assigned as the maximal body weight obtained from day 1 through day 10, and daily body weights were calculated for each day after normalization to this 100% value. The minimum body weight was defined as the lowest body weight after normalization to the 100% value during the span of day 11 until the end of the experiment. Maximal weight loss was calculated by subtraction of the normalized minimum value from the 100% value. Average weight loss was calculated as the average of daily body weight measurements from day 11 until the end of the experiment, subtracted from the 100% maximal body weight.

Statistical Analysis

To determine statistical significance, comparisons among three or more groups were analyzed by use of ANOVA, and comparisons between two groups were analyzed by a Student t test. A P value <0.05 was considered significant. For EAE mean clinical scores and percent initial body weight, error bars represent standard error of the mean (SEM). For all other data, error bars represent standard deviation (SD).

The Concept of a Treg Window.

Figure 1:
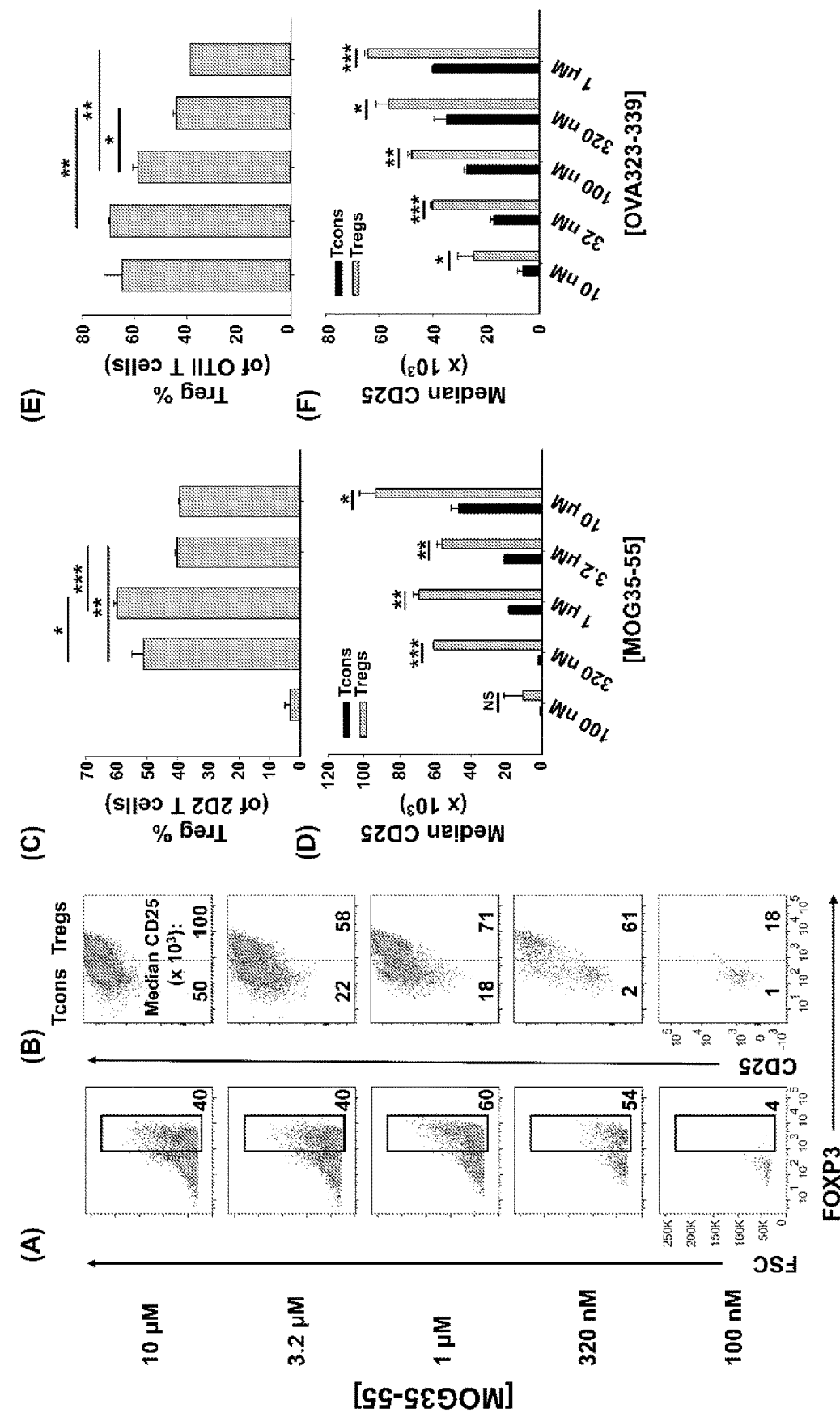
FIG. 1. Intermediate concentrations of antigen induced higher percentages of FOXP3+ Tregs. 2D2-FIG (panels A-D) or OTII-FIG (panels E-F) SPL were activated at a density of 2×10$^6$ cells/ml cRPMI in the presence of 10 nM TGF-β with the indicated concentration of MOG35-55 or OVA323-339. After 3 days, Vβ11+ (2D2) or Vβ5.1+ (OT-II) T cells were analyzed for expression of FOXP3 (panels A, C, E) and CD25 (panels B, D, F). Numbers at the bottom of each dotplot in (panel A) represent the percentages of FOXP3+ T cells, and the numbers in (panel B) represent the median fluorescence intensity of CD25 expression within the FOXP3$^{negative}$ (Tcon) and FOXP3+ (Treg) populations. *p<0.05, p<0.01, *p<0.001. These data are representative of three independent experiments.

To optimize antigen-dependent induction of Tregs, designated concentrations of MOG35-55 were used to activate 2D2-FIG SPL in the presence of 10 nM TGF-β (FIG. 1). 2D2-FIG T cells are specific for MOG35-55 and have an IRES-GFP reporter knock-in immediately downstream of the FOXP3 gene. The CD4$^+$ T cell compartment of 2D2-FIG mice typically contained ≤1% FOXP3$^+$ T cells at steady-state. After 3 days, 320 nM or 1 µM MOG35-55 elicited percentages of FOXP3$^+$ Tregs (54% and 60% respectively) that were significantly higher than the 40% Tregs induced by the higher concentrations of 3.2 µM and 10 µM MOG35-55 (FIG. 1, panels A and C). Thus, the antigen-dependent induction of FOXP3 resembled a bell-shaped curve. MOG-induced FOXP3 expression was entirely dependent upon TGF-β (Wang D, et al. *J Immunol* (2016) 197:2992-3007. Epub 2016/09/14. doi: 10.4049/jimmunol.1500411. PubMed PMID: 27619998). The antigen-dependent expression of CD25 was at least two-fold higher on Tregs than on Tcons, and this difference was maximal at intermediate antigen concentrations of MOG35-55 (320 nM 3.2 µM) (FIG. 1, panels B and D). Similar patterns were noted regarding the concentration dependence of OVA323-339 for CD25 expression on OVA-specific OTII-FIG T cells in the presence of TGF-β (FIG. 1, panels E-F). A lower range of OVA323-339 concentrations was optimal because OT-II T cells have more antigenic potent responsiveness than 2D2 T cells. These data confirm the hypothesis that activated 2D2 and OT-II Tregs exhibit superior CD25 expression compared to Tcon subsets.

To realize the goal of achieving long-term stable growth of FOXP3$^+$ Tregs, we reasoned that an anti-CD25 mAb would differentially block the IL-2 dependent growth and survival of Treg and Tcon subsets. High levels of CD25 were postulated to confer partial resistance to anti-CD25 mAbs among Tregs while completely blocking IL-2 dependent responses of Tcons. Based on this concept, we hypothesized that a 'Treg window' could be operationally defined by adjusting the relative concentrations of IL-2 and anti-CD25 mAb that would favor dominant survival and expansion of Tregs.

The Anti-CD25 PC61 mAb Stabilized Short-Term Treg Cultures.

To test whether an anti-CD25 antibody could be used to enrich Treg lines, 2D2-FIG SPL were activated with MOG35-55 (FIG. 2, panel A, top row), MOG35-55 and TGF-β ($2^{nd}$ row), or MOG35-55, TGF-β, and the anti-CD25 antibody PC61 ($3^{rd}$ row) for 3 days and then passaged into IL-2 containing media (without antigen or TGF-β) in the absence (rows 1-2) or presence (row 3) of PC61. In cultures of TGF-β-induced FOXP3$^+$ Tregs ($2^{nd}$ row), Treg percentages gradually waned during subsequent propagation in IL-2 from a frequency of 47% at day 4 to 19% by day 13. Treg percentage values are given in the bottom right of each panel. In TGF-β-induced cultures that were continuously supplemented with 10 µg/ml (65 nM) of PC61 (bottom row), Treg differentiation was inhibited by PC61 during the initial 3-day activation culture. However, during the subsequent culture with PC61 and IL-2, the Treg frequency increased from 12% on day 4 to 86% by day 13. The elevated Treg frequencies were associated with stronger GFP$^{bright}$ fluorescence which is a correlate of FOXP3 expression (values given at top of each panel). These data indicated that PC61 enabled the selective enrichment of Tregs during propagation in IL-2 over 13 days of culture. Cultures seeded in the absence of TGF-β were used as a reference to gauge the GFP$^+$ window. These data revealed that CD25 was important for the initial induction of Tregs, because PC61 inhibited FOXP3 differentiation in the initial 3-day activation. Conversely, partial blockade of the IL-2/CD25 signaling pathway had the opposite activity in the IL-2 propagation cultures, because PC61 was needed to maintain FOXP3$^+$ Tregs during culture in IL-2. Overall, these data showed that PC61, when used to supplement IL-2 expansion cultures, selected FOXP3$^+$ Tregs as the dominant lineage.

Figure 2:
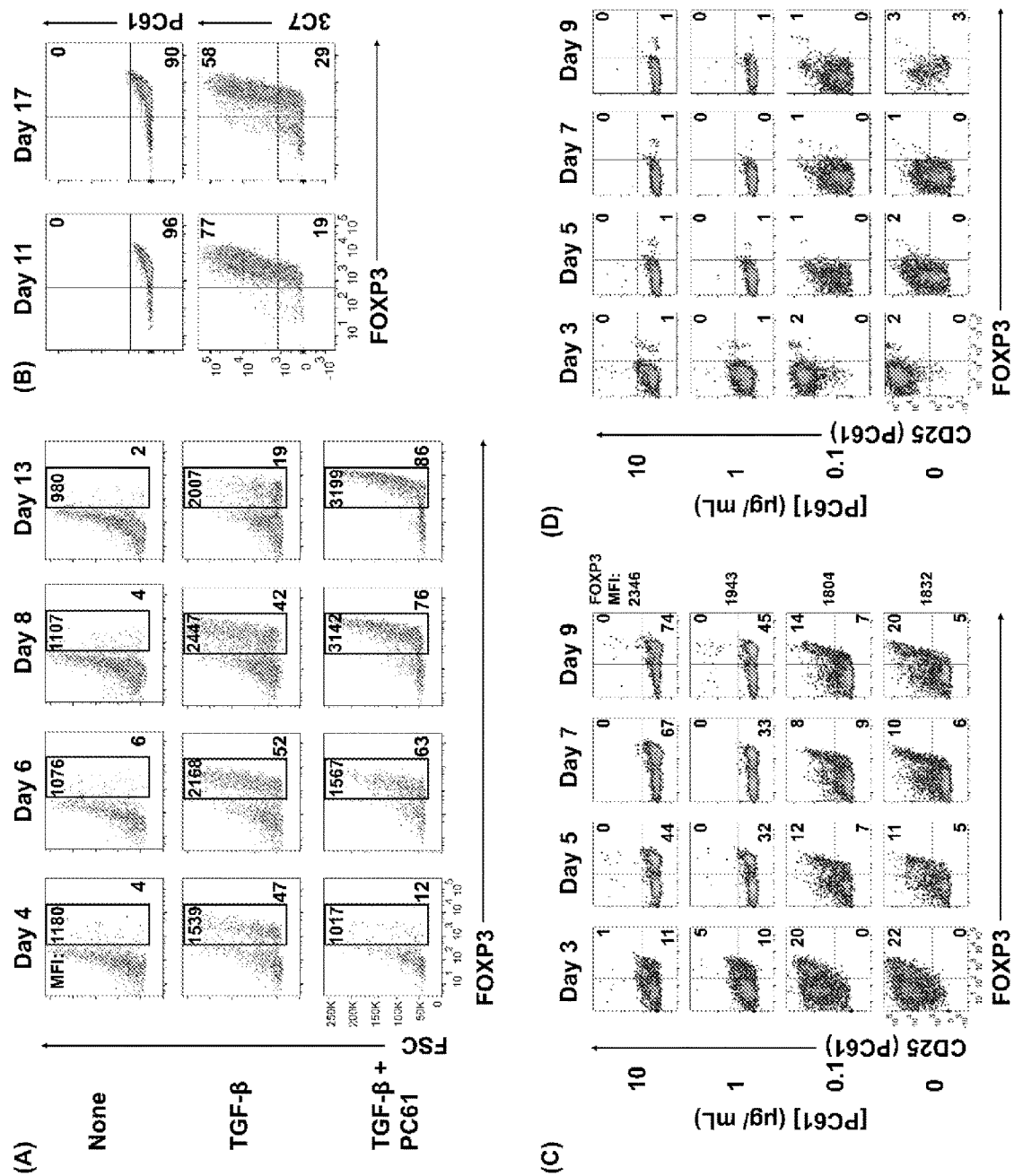
FIG. 2. The anti-CD25 PC61 mAb selectively favored Treg dominance in mixed Treg/Tcon cultures. (panels A-D) 2D2-FIG SPL were activated at a density of 2×10$^6$ cells/ml in cRPMI with MOG35-55 (1 μM) in the presence or absence of TGF-β (10 nM) and/or designated concentrations of PC61 (10 μg/ml; 65 nM, unless designated otherwise). Antigen and TGF-β were present only in the first activation culture and not thereafter. After 3-4 days of activation, cells were passaged at a density of 10$^6$ cells/ml in media containing rat IL-2 with or without PC61. Cultures initiated with PC61 were continued with PC61 during passage into the same conditions every 2-4 days. (panel A) Cells were analyzed on days 4, 6, 8, and 13 post-activation for FOXP3 expression by gating on Vβ11+ cells. The percentage of FOXP3+ Tregs compared to total Vβ11+ cells is indicated in the bottom right of each dotplot. The geometric mean fluorescence intensity (gMFI) of GFP expression is indicated at the top of each gate. (panel B) The initial T cell activation culture did not include PC61, and T cells were then passaged every 3-4 days in rat IL-2 and 10 μg/ml PC61. Vβ11-gated T cells were analyzed on day 11 and 17 for expression of CD25 by PE-conjugated 3C7 or APC-conjugated PC61 anti-CD25 mAb. (panels C and D) The initial activation culture with (panel C) or without (panel D) TGF-β included concentrations of PC61 (10 μg/ml, 1 μg/ml, 0.1 μg/ml, or none) that were maintained throughout the course of the experiment. On days 3, 5, 7, and 9, Vβ11+ T cells were analyzed for FOXP3 expression and for binding of an APC-conjugated anti-CD25 PC61 mAb. These data are representative of three independent experiments.

PC61 lacked cytotoxic activity in vitro, although whether PC61 neutralized or down-modulated CD25 was uncertain. To assess this issue, 2D2-FIG SPL were activated for 3 days with 1 µM MOG35-55 and 10 nM TGF-β and then were passaged every 3-4 days in IL-2 and 10 µg/ml PC61 (FIG. 2, panel B). Again, antigen and TGF-β were not included in the IL-2 expansion phase of these experiments. Analyses on days 11 and 17 revealed that the line was almost entirely comprised of FOXP3$^+$ Tregs (>90%). A PE-conjugated 3C7 anti-CD25 mAb, which recognizes a site on CD25 distinct from the PC61 epitope, revealed high levels of CD25 on these Tregs despite the continuous culture in PC61 and the saturation of CD25 with PC61 (FIG. 2, panel B, bottom images). Conversely, an APC-conjugated PC61 did not bind CD25 because PC61-specific epitopes on CD25 were saturated with unlabeled PC61 mAb that had bound CD25 during the culture phase (FIG. 2, panel B, top images). These data indicate that PC61 facilitates Treg selection, at least in part, by functional neutralization of CD25 in vitro.

An important question was whether Treg enrichment required PC61-mediated saturation of CD25 (FIG. 2, panel C). To assess this question, 2D2-FIG T cells were activated for 3 days with MOG35-55 and TGF-β in the presence or absence of designated PC61 concentrations. As noted before, high concentrations of PC61 inhibited Treg induction when assessed on day 3. The T cells were then passaged into IL-2 on day 3 with the same PC61 concentrations but without antigen or TGF-β. On days 5 through 9, concentrations of 1 and 10 µg/ml PC61 nearly saturated CD25 as determined by a lack of surface labeling by an APC-conjugated PC61 mAb (y-axis), because pre-existing PC61-CD25 complexes prevented the binding of APC-conjugated PC61. These PC61 concentrations (1 and 10 µg/ml) respectively facilitated Treg enrichment to frequencies of 45% and 74%. PC61 dose dependently augmented GFP MFI (mean fluorescence intensity; 4 digit number on the right of rightmost column) on day 9 and thereby supported the hypothesis that PC61 preferentially selected mature Tregs. In the presence of 0.1 µg/ml PC61 or in control cultures without PC61, Tregs and Tcons expressed high levels of free CD25, and Treg frequencies were sparse at approximately 20% throughout the 9 days of culture. Importantly, PC61 by itself did not induce FOXP3, as T cells activated without TGF-β and cultured in the presence of PC61 did not result in Tregs (FIG. 2, panel D). These data indicate that TGF-β-induced Tregs continuously required saturating PC61 concentrations during propagation in IL-2 to engender high percentages of Tregs.

Figure 3:
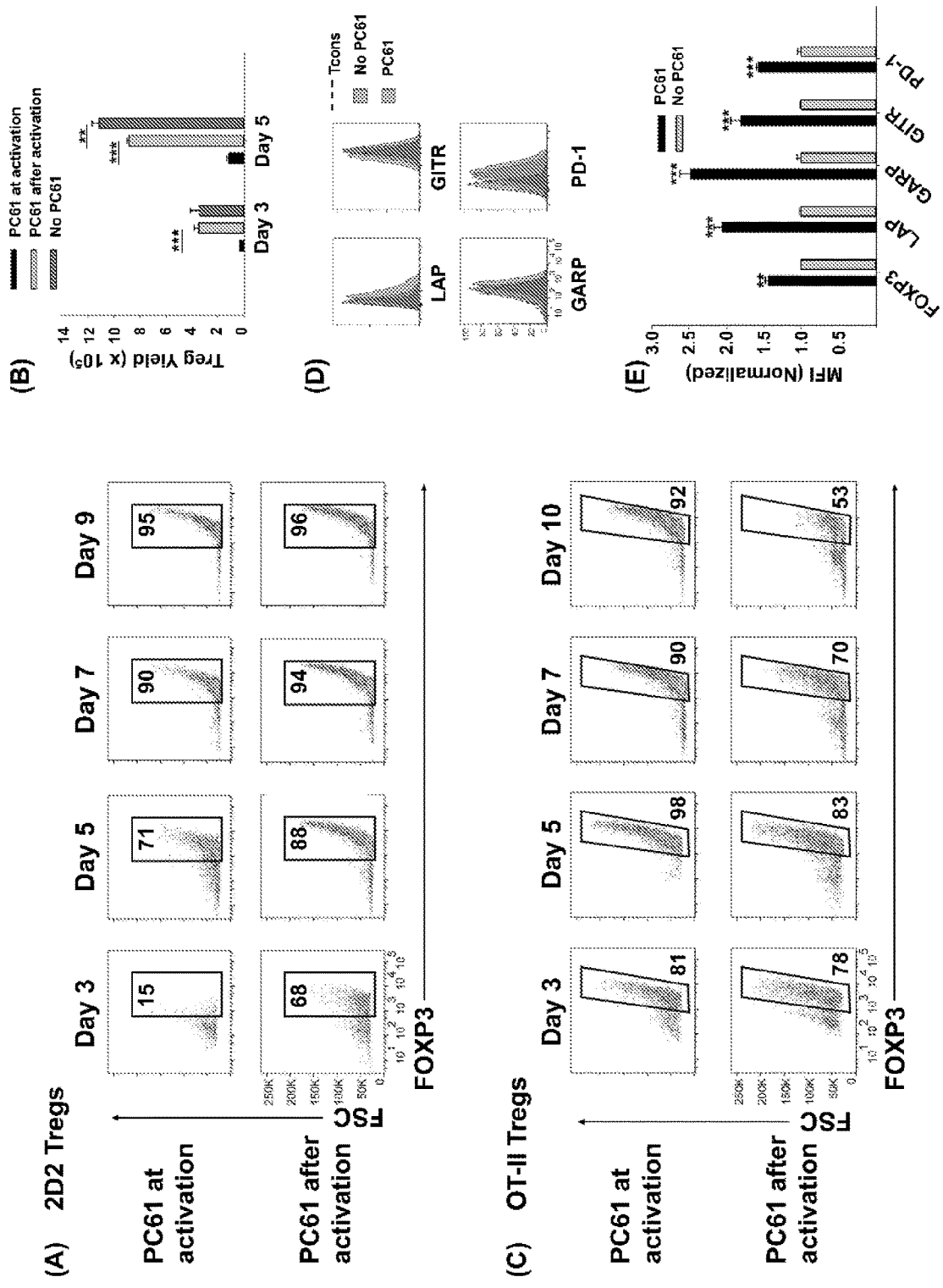
FIG. 3. PC61 allowed for rapid generation of pure Treg lines. 2D2-FIG SPL (panels A-B, D-E) or OTII-FIG SPL (panel C) were activated at a density of 2×10$^6$ cells/ml in cRPMI with MOG35-55 (1 μM) or 100 nM OVA323-339 respectively with 10 nM TGF-β in the presence or absence of 10 μg/ml PC61. Antigen and TGF-β were present only in the initial 3-day activation culture and not thereafter. (panels A-C) PC61 was (PC61 at activation) or was not (PC61 after activation) included in the initial 3-day activation culture but was included in both groups after passage of the cells on day 3. Cells were counted and then analyzed to determine percentages of viable, Vβ11+ (2D2), Vβ5.1+ (OTII), FOXP3+ T cells on the designated days. (panel B) Shown are the 2D2-FIG Treg yields on days 3 and 5. (panels D-E) After 3 days of activation with or without PC61, 2D2-FIG T cells were passaged for 10 days at a density of 10$^6$ cells/ml in rat IL-2 in the presence or absence of 10 μg/ml PC61. Cells gated as Vβ11+ FOXP3+ Tregs or FOXP3$^{negative}$ Tcons were analyzed for expression of LAP, GARP, GITR, and PD-1 on day 10 post-activation. MFI Values were normalized so that values obtained from T cells cultured in the absence of PC61 was equal to 1. These experiments are representative of three independent experiments.

Although PC61 stabilized Tregs in IL-2 maintenance cultures, inclusion of PC61 in the initial 3-day activation culture appeared to delay Treg induction. To assess this issue, PC61 was or was not included in the initial 3-day activation culture together with 2D2-FIG SPL, MOG35-55, and TGF-β (FIG. 3, panel A), and then PC61 was included in the IL-2 maintenance cultures of both groups through day 9. Regardless of whether PC61 was added on day 0 (PC61 at activation) or day 3 (PC61 after activation), PC61 facilitated the emergence of highly enriched FOXP3$^+$ Tregs by day 9. However, introduction of PC61 after the initial activation culture was advantageous because this regimen resulted in the accelerated enrichment of Tregs as noted by differences at days 3-5 (FIG. 3, panel A) and increased Treg yields at day 5 (FIG. 3, panel B). Treg yield on day 5 post-activation was more than 7-fold higher in the "PC61 after activation" group compared to "PC61 at activation" group. Cultures that lacked PC61 in both phases of culture (No PC61) resulted in a dramatic reduction in Treg percentages but similar cell yields compared to the "PC61 after activation" group. Interestingly, PC61 was necessary at activation and during propagation to generate highly pure, stable OT-II Treg lines (FIG. 3, panel C). This phenomenon is most likely due to the high responsiveness of OT-II T cells to their cognate antigen (OVA323-339). That is, PC61-mediated inhibition was needed earlier in the activation cascade due to the higher antigen reactivity of OT-II T cells. Thus, the requirement for the anti-CD25 mAb during the initial culture for OTII-FIG T cells may reflect the antigenic potency of the cognate antigen. Nevertheless, 2D2 and OT-II FOXP3$^+$ enriched lines were obtained without physical purification or any genetic modification by the end of the experiment. These findings indicated that the presence of PC61 during the IL-2 expansion phase was important for achieving high Treg percentages in stable FOXP3$^+$ Treg lines.

To assess whether PC61 affected expression of selected Treg markers, 2D2-FIG SPL were subjected to a 3-day activation with MOG35-55 and TGF-β (FIG. 3, panels D, E). The T cells were then passaged every 3-4 days in IL-2 for an additional 10 days in the presence or absence of PC61, whereby the lines were almost exclusively small, rested T cells. Gated Treg and Tcon subsets were analyzed separately. PC61-cultivated Tregs differed from control (no PC61) cultures via higher Treg expression of FOXP3, LAP, GARP, GITR, and PD-1. These data revealed that PC61-maintained Tregs had markers consistent with the Treg lineage and expressed significantly higher levels of these markers compared to Tregs cultivated in the absence of PC61, signifying the ability of PC61 to select mature Tregs.

Figure 4:
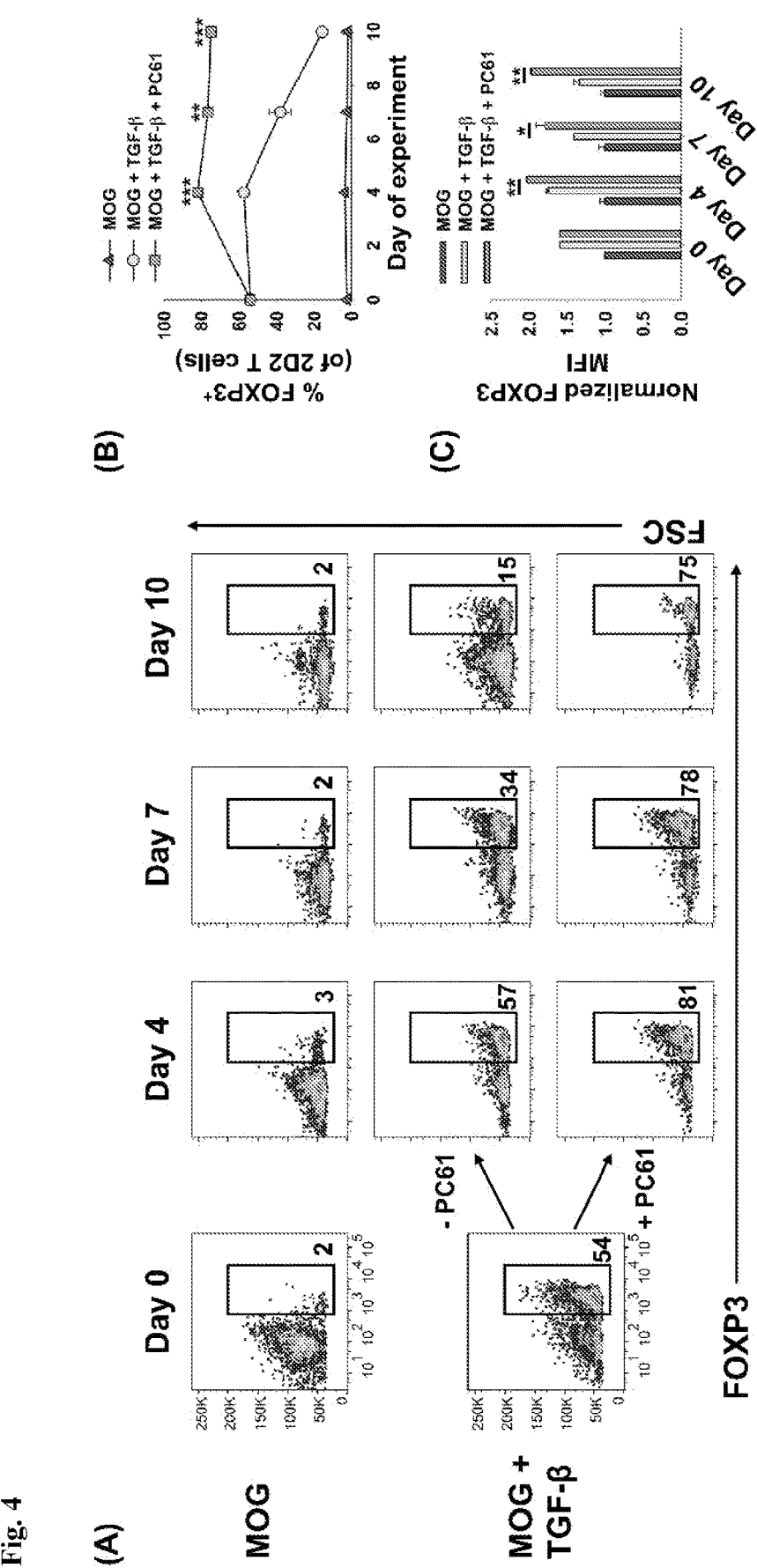
FIG. 4. PC61 enabled the preferential outgrowth of TGF-β-induced iTregs from 2D2-FIG Rag1$^{-/-}$ mice. 2D2-FIG Rag1$^{-/-}$ mice SPL were activated for 4 days at a density of 2×10$^6$ cells/ml in cRPMI with MOG35-55 in the presence or absence of 1 nM TGF-β to generate Tregs and Tcons, respectively, and were passaged at a density of 5×10$^5$ cells/ml cRPMI with rat IL-2 on day 0 of the rest phase. T cells were then passaged with or without PC61 (10 μg/ml) (in the absence of TGF-β and MOG) as designated every 2-4 days. Vβ11$^+$ T cells were assessed for FOXP3 expression on days 0, 4, 7, and 10 after activation. Shown are representative dot plots of the percentage of FOXP3$^+$ Tregs in the Vβ11$^+$ T cell population (panel A) and the corresponding averages of triplicate samples (panel B). The bar graph shows the geometric MFI of FOXP3 expression in the FOXP3$^+$ gate. The gMFI was normalized so that the FOXP3 MFI of Tregs activated in the absence of TGF-β was equal to 1. *p<0.05, p<0.01, *p<0.001. These experiments are representative of three independent experiments.

An important question was whether iTregs that were induced de novo during activation in the presence of TGF-β were stabilized by PC61, because iTregs may be important starting material for derivation of antigen-specific Tregs. Previous experiments however were initiated with total 2D2-FIG SPL, which may include pre-existing thymically-derived tTregs that may contribute or dominate growth in the presence of PC61. In 2D2-FIG mice, pre-existing Tregs typically comprise less than 1% of CD4$^+$ T cells, with a frequency range of approximately 0.2-1.5% pre-existing FOXP3$^+$ Tregs. To assess this issue, Tregs were induced with MOG and TGF-β from 2D2-FIG Rag1$^{-/-}$ mice, which lack tTregs (FIG. 4). 2D2-FIG Rag1$^{-/-}$ Tregs were cultured in the presence of IL-2 with or without PC61. Tregs cultured in the presence of PC61 showed a stable, high percentage of Tregs (>75%); whereas, Tregs cultured in the absence of PC61 showed a diminishing Treg percentage throughout the duration of the experiment (FIG. 4, panels A, B). The FOXP3 gMFI of Tregs cultured in the presence of PC61 was significantly higher than the gMFI of Tregs cultured in the absence of PC61 (FIG. 4, panel C). These data provide evidence that PC61 stabilizes outgrowth TGF-β-induced iTregs.

PC61 was the Anti-CD25 mAb of Choice for Blockade of IL-2 Signaling and Selection of Tregs.

Figure 5:
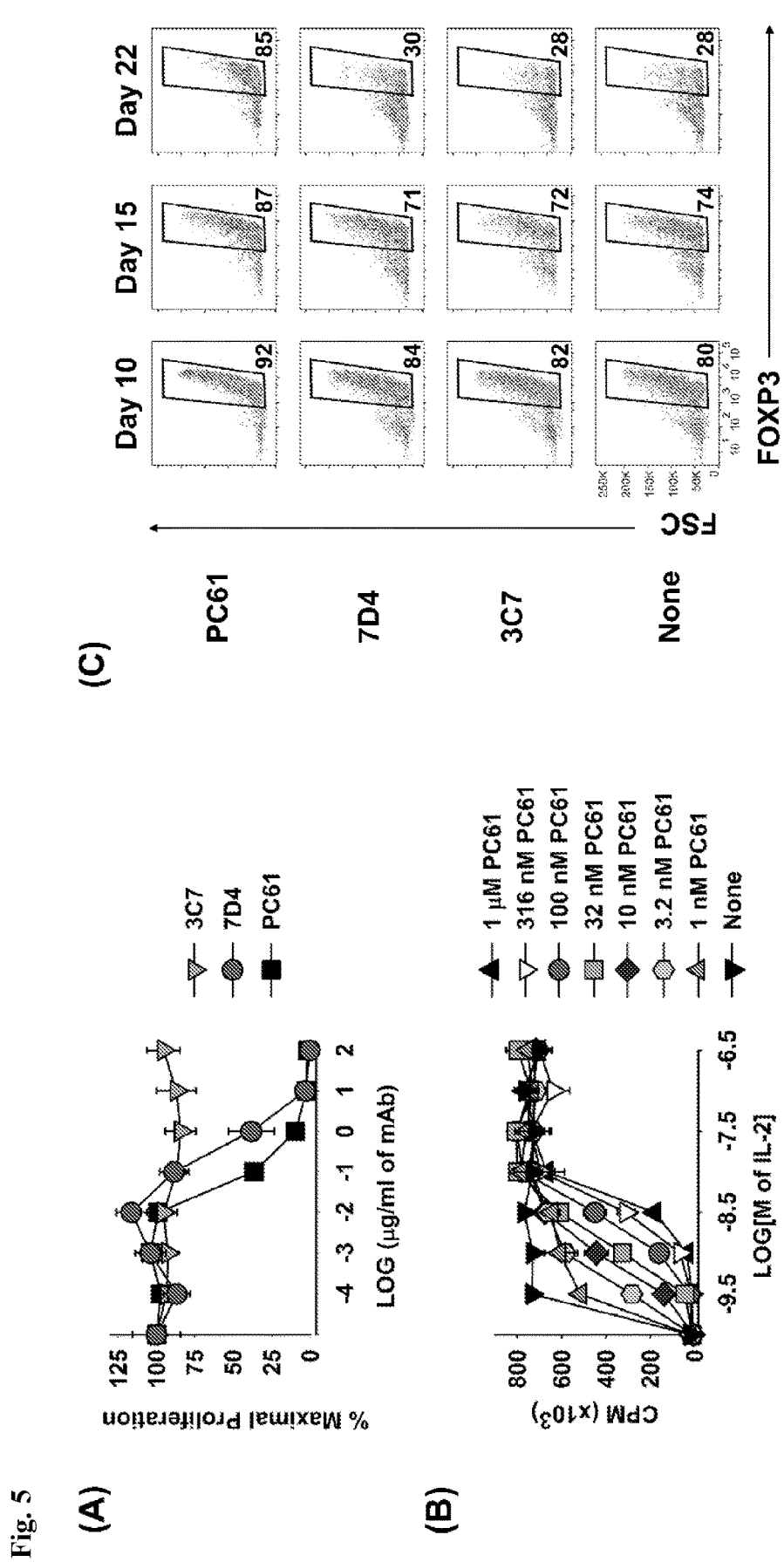
FIG. 5. The PC61 anti-CD25 mAb was a functional antagonist of IL-2 growth at low concentrations of IL-2 and was superior to the 7D4 and 3C7 anti-CD25 mAbs for maintenance of Tregs. (panels A-B) A continuously-propagated line of IL-2 dependent CD4$^+$ T cells (SJL-PLP.1 T cells) was used as IL-2 responders in these assays. These T cells (3,000/well) were cultured with rat IL-2 and designated concentrations of PC61, 7D4, or 3C7 mAbs (panel A) or were cultured with designated concentrations of purified PC61 and mouse IL-2 (panel B). Cells were pulsed with [$^3$H]thymidine during the last 24 hrs of a 3-day culture. (panel C) 2D2-FIG SPL were activated at a density of 2×10$^6$ cells/ml cRPMI with 1 μM MOG35-55 in the presence of 10 nM TGF-β. After 3 days, cells were passaged at a density of 10$^6$ cells/ml with IL-2 plus 10 μg/ml PC61, 7D4, 3C7, or no anti-CD25 mAb. Cells were passaged every 3-4 days in IL-2 with the same anti-CD25 antibody. Vβ11$^+$ T cells were analyzed for FOXP3 expression on days 10, 15, and 22. These experiments are representative of three independent experiments.

Because anti-CD25 mAbs differ in epitope specificity and inhibitory mechanism, three anti-CD25 mAb were screened for inhibitory efficacy in assays of IL-2 dependent T cell growth. The PC61 mAb (rat IgG1λ) was more suppressive than the 7D4 mAb (rat IgM, κ) whereas the 3C7 mAb (rat IgG2b, κ) lacked inhibitory activity at this concentration of IL-2 (FIG. 5, panel A). PC61 may have superior efficacy because PC61 and IL-2 bind distinct sites on the CD25 IL-2Rα, and PC61 facilitates the dissociation of IL-2, but not vice versa (Lowenthal J W, et al. *J Immunol* (1985) 135(6):3988-94. PubMed PMID: 3934270). Although PC61 is routinely used for depletion of Tregs in vivo (Setiady Y Y, et al. *Eur J Immunol* (2010) 40(3):780-6. doi: 10.1002/eji.200939613. PubMed PMID: 20039297), the PC61 mAb had no cytolytic or depleting activity in vitro, as shown previously in FIG. 2. PC61 mediates Treg depletion in vivo via FcγR-mediated clearance (Setiady Y Y, et al. *Eur J Immunol* (2010) 40(3):780-6. doi: 10.1002/eji.200939613. PubMed PMID: 20039297), but this mechanism was not operational in T cell cultures.

As shown in FIG. 5, panel B, PC61 and IL-2 exhibited functional competition in cultures of a transformed Tcon line that expressed a CD25$^{high}$ phenotype and potent IL-2 responsiveness. High concentrations of PC61 (up to 1 µM) inhibited IL-2 responses in the presence of limiting IL-2 concentrations (<10 nM) as shown by right-shifted IL-2 concentration-response curves. In contrast, high concentrations of IL-2 (>10 nM) overwhelmed the inhibitory action of all tested concentrations of PC61. High concentrations of IL-2 may signal through lower affinity IL2Rβ-γ complexes and thereby may drive IL-2 dependent growth independent of CD25. Overall, these data indicate that PC61 effectively inhibited IL-2 responses, but only within a range of relatively low IL-2 concentrations.

Based on its superior IL-2 inhibitory activity (FIG. 5, panel A), PC61 was more efficient than the anti-CD25 mAb 7D4 and 3C7 for maintenance of Treg cultures (FIG. 5, panel C). Due to the superior inhibitory efficacy and superior Treg selectivity, the anti-CD25 PC61 mAb was used for the remainder of the study.

PC61 Enabled the Dominant Outgrowth of Tregs in Mixed Treg/Tcon Cultures.

Figure 6:
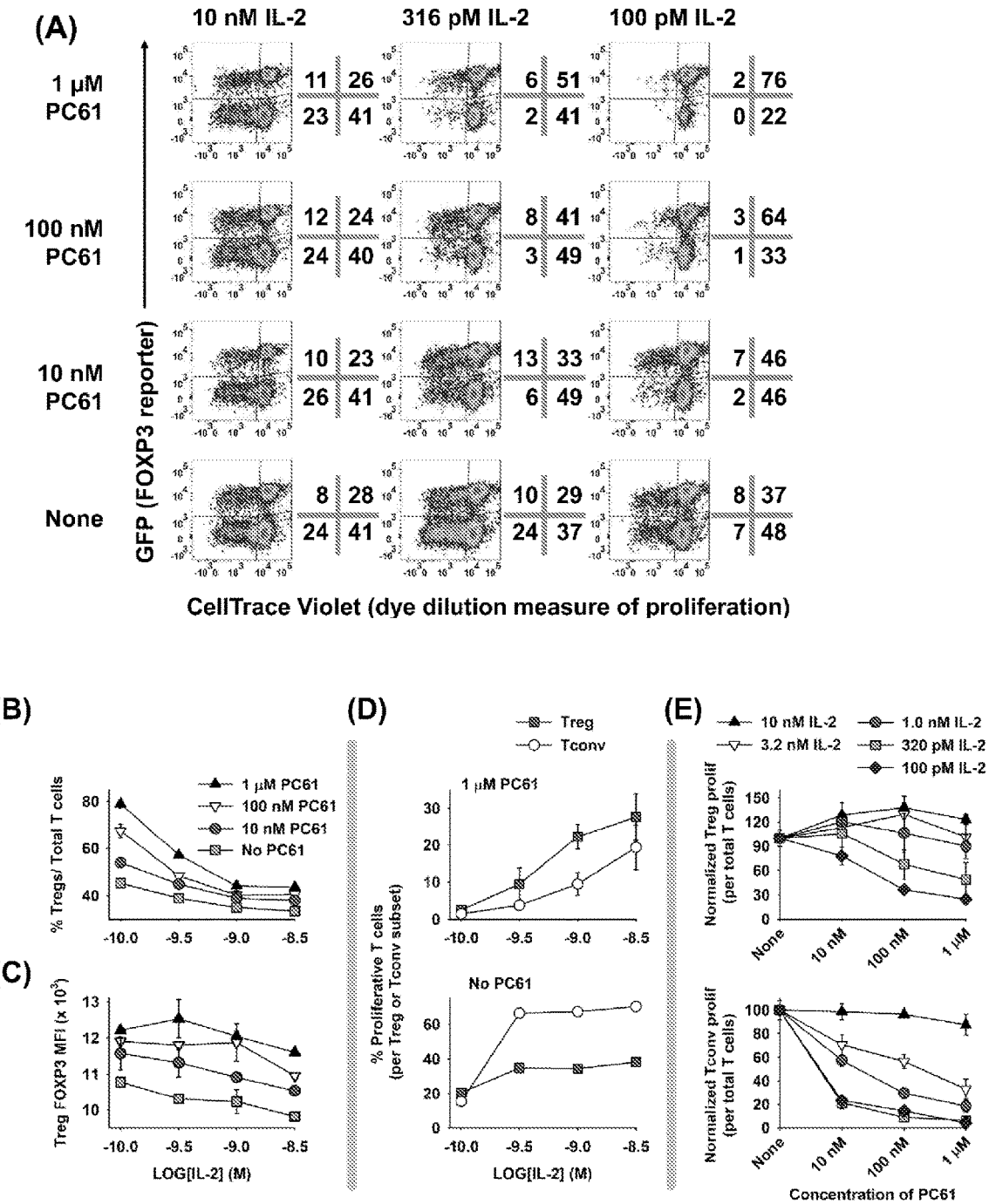
FIG. 6. A permissive 'Treg window' that favored dominance of FOXP3$^+$ Tregs was defined by low IL-2 concentrations and high PC61 concentrations. 2D2-FIG T cells were cultured with 1 μM MOG35-55 for 4 days in the presence or absence of 10 nM TGF-β to establish lines of FOXP3$^+$ Tregs and FOXP3$^{negative}$ Tcons, respectively. T cells were passaged every 3 or 4 days for a total 16 days in IL-2, and Treg cultures were also supplemented with 10 μg/ml PC61 to select and establish high percentages of FOXP3$^+$ Tregs. At the initiation of the experiment, Tregs and Tcons were equally mixed and labelled with CTV and were cultured for 6 days in designated concentrations of IL-2 (100 pM 10 nM) in the presence or absence of designated concentrations of PC61. Dotplots in (panel A) show proliferating (left quadrants) versus non-proliferating (right quadrants) Tregs (top quadrants) and Tcons (bottom quadrants). Shown are percentages (panel B) and MFI (panel C) of FOXP3$^+$ Tregs in the Vβ11+ population. (panel D) Shown are the percentages of proliferating FOXP3$^+$ Tregs and FOXP3$^{negative}$ Tcons in the presence or absence of 1 μM PC61. (panel E) Normalized proliferation of Tregs and Tcons at designated concentrations of IL-2 and PC61. This experiment is representative of three independent experiments.

The concept of a Treg window was tested with mixed 2D2 (MOG-specific) lines of FOXP3$^+$ and FOXP3" T cells (FIG. 6). These T cells were propagated in IL-2 for 16 days before use in this assay, so that Tregs represented nearly 96% of the T cells in the FOXP3$^+$ line. Equal numbers of Tcons and Tregs were labeled with CellTrace Violet (CTV) and were cultured for 6 days with designated concentrations of IL-2 and PC61. This analysis distinguished proliferative subsets (left quadrants) from non-proliferative subsets (right quadrants) as well as Tregs (upper quadrants) from Tcons (lower quadrants) (FIG. 6, panel A). Shown are two relatively low IL-2 concentrations (100 pM and 316 pM) in which proliferative and non-proliferative Tregs were dominant (exhibited higher percentages) compared to Tcons when cultured with 1 µM PC61. At 100 pM IL-2 and either 1 µM PC61 or 'no PC61', 78% or 45% of T cells (sum of upper two quadrants) were Tregs, respectively. At 316 pM IL-2, proliferative Tregs exhibited higher frequencies than proliferative Tcons in the presence but not absence of 10 nM, 100 nM, and 1 µM PC61. At high IL-2 concentrations (e.g. 10 nM), Tcons were dominant and showed overgrowth regardless of PC61 concentration. The concentration-dependent ability of PC61 to promote Treg dominance in low IL-2 concentrations (FIG. 6, panel B) correlated with preservation of high GFP fluorescence (FIG. 6, panel C), which is an indirect measure of FOXP3 expression on a per cell basis. Tregs were dominant within a 10-fold range of IL-2 concentrations (320 pM 3.2 nM, FIG. 6, panel D) in the presence of 1 µM PC61 whereas Tcons were dominant at the same IL-2 concentrations in the absence of PC61. Although PC61 exhibited concentration-dependent inhibition of IL-2 dependent Treg growth, PC61 was a more potent inhibitor of Tcon growth at limiting IL-2 concentrations, such that differential growth and survival favored persistence of Tregs over Tcons (FIG. 6, panel E). Overall, these data reveal a 'Treg window' defined by ranges of IL-2 and PC61 concentrations that enabled dominant survival and outgrowth of FOXP3$^+$ Tregs.

The Anti-CD25 PC61 Antibody Enabled Maintenance of Long-Term Lines of FOXP3$^+$ Tregs.

Figure 7:
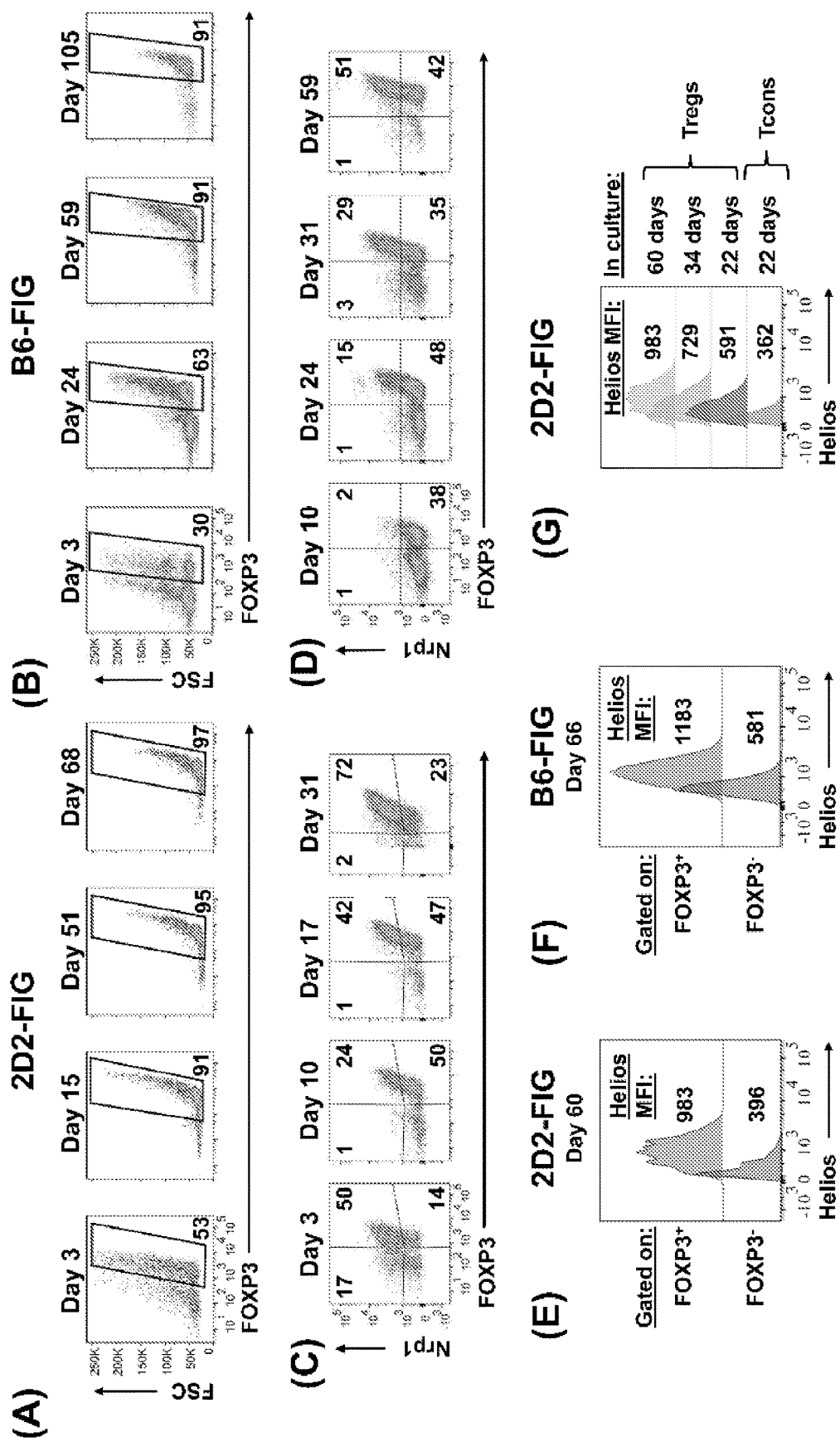
FIG. 7. The anti-CD25 mAb PC61 enabled long-term, stable propagation of FOXP3$^+$ Tregs. 2D2-FIG SPL or FIG SPL were activated with 1 μM MOG35-55 or 2.5 μg/ml Con-A, respectively, at a density of 2×10$^6$ SPL/ml in the presence of 10 nM TGF-β. After 3 days of activation, cells were passaged at a density of 10$^6$ cells/ml in media containing rat IL-2 and 10 μg/ml PC61. Cells were passaged every 3-4 days in the same conditions for the indicated durations. In 2D2-FIG cultures, Vβ11$^+$ T cells were analyzed on the indicated days for FOXP3 expression (panel A), Neuropilin-1 expression (panel C), and Helios expression (panels E and G). (panel A) and (panel C) represent analyses of lines established from separate mice. (panels B, D, F) In C57BL/6 (B6)-FIG cultures, CD4$^+$ T cells were purified to remove CD8$^+$ T cells. FIG. lines were analyzed for FOXP3 expression (panel B), Neuropilin expression (panel D), and Helios expression (panel F). For (panel E) and (panel F), Helios expression was measured in the FOXP3$^+$ and the FOXP3$^{negative}$ populations from the same line. These experiments are representative of three independent experiments.

Given that PC61 was instrumental in selecting enriched FOXP3$^+$ Treg lines over a 2-3 week timespan (FIG. 2), a question was whether PC61 also allowed maintenance of highly enriched Treg lines over the course of months. To assess this question, 2D2-FIG SPL were activated with MOG35-55 and TGF-β in a 3-day activation in the absence of PC61 and were then passaged every 3-4 days in IL-2 with 10 µg/ml PC61 (FIG. 7, panel A). Over the course of 68 days, the line was analyzed for percentages of FOXP3$^+$ Tregs. Tregs represented over 90% of the cells by day 15 and persisted at these levels throughout the duration of the culture without showing any signs of attenuation. Equivalent lines propagated in IL-2 but in the absence of PC61 showed progressive loss and extinction of FOXP3$^+$ Tregs across 2-4 weeks of propagation in IL-2 (e.g., FIG. 2).

FOXP3$^+$ Treg lines from naïve, clonotypically-diverse FIG SPL could also be derived by addition of PC61 to IL-2 expansion cultures (FIG. 7, panel B). Naïve FIG SPL were activated for 3 days with Con-A and TGF-0 and then were propagated in IL-2 in the presence of PC61. CD4$^+$ T cells were purified to remove CD8$^+$ T cells in polyclonal FIG SPL cultures to prevent CD8$^+$ T cell overgrowth of the line, but CD4$^+$ T cell purification was not necessary for 2D2-FIG Tregs given that 2D2-FIG mice largely lacked CD8$^+$ T cells. Over the course of 105 days, cultures became progressively enriched with polyclonal FOXP3$^+$ Treg cells until over 90% of the line was comprised of FOXP3$^+$ Tregs. In subsequent polyclonal FIG Treg lines, CD4 purification was performed on day 4 post-activation as opposed to day 10. This earlier intervention allowed for the generation of Treg lines consisting of >90% Tregs by day 10 (not shown). Culture of Treg lines in IL-2 expansion cultures with PC61 resulted in a slow and steady expansion of cell numbers. These findings reveal the generalized applicability of PC61-mediated Treg selection in mice. The implication is that Treg lines can be generated and maintained indefinitely in the presence of PC61. We have generated at least 15 different 2D2-FIG Treg lines, 5 different OT-II Treg lines, and 4 different polyclonal Treg lines and carried them for more than 50 days with Treg percentages greater than 85% of the T cell population. Overall, these lines showed no loss of Treg percentages and no decrement in GFP fluorescence (i.e., FOXP3 expression) over the entire culture duration.

These long-term lines expressed Neuropilin-1 and Helios, which have been associated with the FOXP3$^+$ Treg phenotype (FIG. 7, panels C-G). Neuropilin-1 was expressed on both 2D2-FIG Tregs (FIG. 7, panel C) and polyclonal Tregs (FIG. 7, panel D). Neuropilin-1 exhibited progressive increases in MFI as a function of time such that Neuropilin-1 expression was positively correlated with the longevity of culture. Given that Helios is a transcription factor implicated in Treg function, we also analyzed 2D2-FIG Tregs on day 60 of culture (FIG. 7, panel E) and polyclonal Tregs on day 66 of culture (FIG. 7, panel F) for expression of Helios. 2D2-FIG Tregs and polyclonal Tregs both expressed Helios whereas Tcons lacked detectable expression. Like Neuropilin-1, Helios expression levels correlated with the duration of culture (FIG. 7, panel G). These findings provided evidence that expression of both Neuropilin-1 and Helios were amplified by continuous, low-intensity IL-2 signaling in continuity with Treg lineage commitment.

Re-Activation and Expansion of FOXP3$^+$ Treg Lines.

Figure 8:
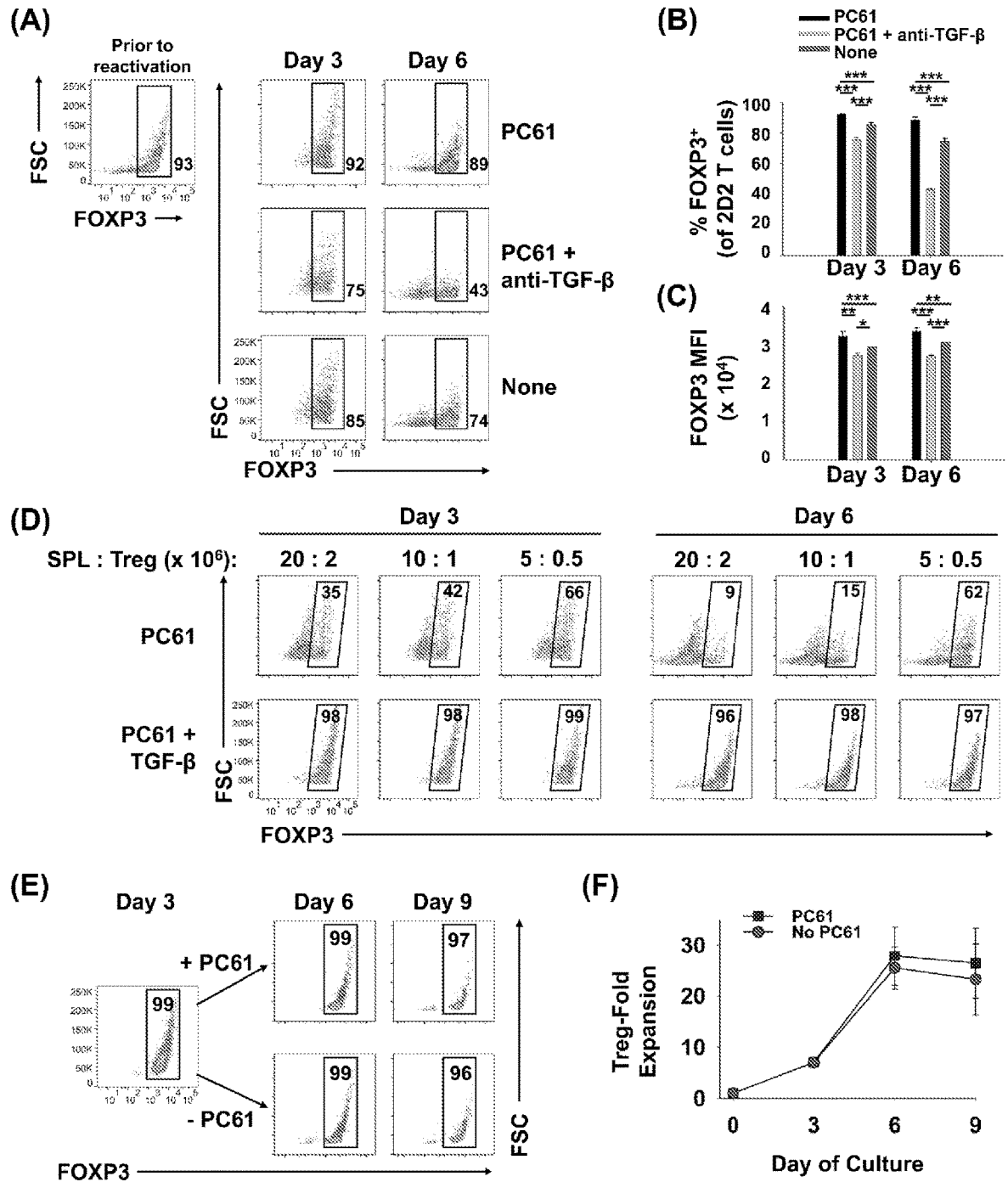
FIG. 8. TGF-β was required for the maintenance of Treg stability during secondary Treg activation and expansion. (panels A-C) 100,000 Tregs (rested for 23 days, 93% FOXP3$^+$) and 10$^6$ irradiated splenic APC were cultured in 200 μl with 1 μM MOG35-55 and IL-2 with or without 10 μg/ml PC61 and the 1D11 anti-TGF-β mAb (50 μg/ml) as designated. Cells were analyzed on days 3 and 6 of activation. (panel A) FOXP3$^+$ Treg percentages are shown in bottom right corner for the Vβ11$^+$2 D2 TCR-gated population. Also shown are the average percentages of FOXP3$^+$ Tregs per Vβ11$^+$ T cells (panel B) and average FOXP3 (GFP) MFI (panel C). Error bars represent standard deviations. *p<0.05, p≤0.01, *p≤0.001. (panel D) Tregs that were rested for 33 days (94% FOXP3$^+$) were re-activated with irradiated SPL and 1 μM MOG35-55 in the presence of 10 μg/ml PC61 with (bottom row) or without (top row) 100 pM TGF-β. Activation cultures contained rat IL-2 with designated densities of Tregs and irradiated splenic APC in 5 ml media as indicated above each set of dotplots. For example, 20×10$^6$ irradiated SPL were used to activate 2×10$^6$ Tregs. Alternatively, 10×10$^6$ or 5×10$^6$ APC were used to activate 10$^6$ or 5×10$^5$ Tregs, respectively, in a 5 ml volume. Cells were analyzed on days 3 and 6 of activation by gating on Vβ11$^+$ T cells. Percentages of FOXP3$^+$ T cells are shown in the top right corner of each dotplot. (panels E,F) 250,000 2D2 iTregs were induced by culturing FACS-sorted naïve FOXP3$^{negative}$ T cells with 50,000 irradiated bone marrow-derived dendritic cells, 2.5 μg/ml Con-A, IL-2, and 1 nM TGF-β. T cells were passaged into IL2 with or without 10 μg/ml PC61 on day 3 and were subsequently passaged again on day 6 at a density of 5×10$^5$ cells/ml. Cells were counted by Trypan Blue exclusion and analyzed by flow cytometry for FOXP3 expression on Vβ11+ gated T cells. Cell yields (panel F) were calculated by multiplying cell counts by the percentage of Vβ11$^+$ FOXP3$^+$ T cells on days 3, 6, and 9. These experiments are representative of three independent experiments.

We assumed that re-activation of FOXP3$^+$ Treg lines would be needed for Treg-mediated suppressive activity in adoptive transfer experiments. The issue was whether FOXP3$^+$ Tregs could undergo secondary activation in vitro without loss of FOXP3 and the Treg phenotype. Like the primary activation, we hypothesized that re-activation of established Treg lines would be contingent on TGF-β. To assess this issue, a 2D2-FIG. line (>90% FOXP3$^+$ Tregs) that had been cultured for 23 days in IL-2 and PC61 was reactivated for 3 or 6 days with irradiated splenic APC and MOG35-55 in the presence of IL-2 with or without PC61 and the neutralizing anti-TGF-β 1D11 mAb (FIG. 8, panel A-C). The presence of PC61 during secondary activation stabilized Treg percentages at approximately 90% (FIG. 8, panel A top row; FIG. 8, panel B). The presence of PC61 also stabilized FOXP3 expression, as reflected by GFP MFI (FIG. 8, panel C). Notably, 1D11-mediated neutralization of TGF-β resulted in a loss of FOXP3+ Treg percentages to less than 50% and a decrement in FOXP3 expression on a per cell basis, as reflected by the GFP MFI (FIG. 8, panel A middle row; FIG. 8, panel C). These data indicate that FOXP3 expression during antigen-driven cellular activation was maintained by TGF-β produced by cells in the culture.

These data provided evidence that exogenous TGF-β might augment Treg stability in subsequent re-activation cultures. To assess this issue, designated cell densities were used at a constant 10:1 APC: Treg ratio at $4 \times 10^5$ Tregs/ml, $2 \times 10^5$ Tregs/ml, or $10^5$ Tregs/ml (FIG. 8, panel D and Table 1). In the absence of exogenous TGF-β, T cells underwent activation and expansion at each density (Table 1), but Treg percentages declined, particularly at higher cell densities. Most likely, high T cell densities caused a more robust activation and perhaps enhanced the production of pro-inflammatory cytokines (i.e., IL-23 or GM-CSF) that might antagonize the action of TGF-β. Notably, the presence of exogenous TGF-β prevented decrement of Treg frequencies and stabilized the Treg phenotype regardless of the cell density. Based on cell counts, high initial cell densities in the presence of TGF-β enabled the most robust expansion of Tregs by day 3 of activation (Table 1). These data indicate that optimal Treg expansion requires the presence of exogenous TGF-β during secondary activation. This observation is key to strategies for expansion of continuous FOXP3+ Treg

TABLE 1

Tregs exhibit stable expansion in the presence of exogenous TGF-β, IL-2, and PC61.

| Group[a] | APC: Treg # ($\times 10^6$) on day 0 | Cell # ($\times 10^6$) on day 3 | Treg # ($\times 10^6$) on day 3 | Treg yield[b] | FOXP3+ Treg percentages |
|---|---|---|---|---|---|
| No TGF-β | 20: 2 | 9.58 | 3.40 | 1.7 | 35 |
| | 10: 1 | 3.33 | 1.44 | 1.4 | 42 |
| | 5: 0.5 | 2.20 | 1.48 | 3.0 | 66 |
| TGF-β | 20: 2 | 13.36 | 13.13 | 6.6 | 98 |
| | 10: 1 | 5.26 | 5.18 | 5.2 | 98 |
| | 5: 0.5 | 2.16 | 2.13 | 4.3 | 99 |

[a]T cells were rested for 33 days and were 94% FOXP3+ Tregs at the initiation of the experiment. T cells were activated with irradiated SPL, 1 μM MOG35-55, rat IL-2, and 10 μg/ml PC61 and in the presence or absence of 100 pM TGF-β. Cultures were setup in 5 ml media containing designated numbers of Tregs and irradiated SPL (column 2).
[b]Cells were analyzed on day 3 of activation by gating on Vβ11 and FOXP3 (GFP). Absolute cell counts (trypan blue exclusion), Vβ11+ T cell percentages, and FOXP3+ Treg percentages were used to calculate Treg numbers. Treg yield was calculated by dividing the Treg cell count on day 3 by the starting Treg count ($2 \times 10^6$, $1 \times 10^6$, or $0.5 \times 10^6$) on day 0. These data are representative of three independent experiments.

To quantitate Treg expansion, an established, long-term 2D2-FIG Treg line was activated for 3 days with irradiated bone marrow-derived dendritic cells, 2.5 μg/ml Con-A, 1 nM TGF-β, and IL-2 (FIG. 8, panels E, F). T cells were then passaged on days 3 and 6 at a density of $5 \times 10^5$ cells/ml cRPMI containing rat IL-2 with or without PC61. Viable cells were enumerated (Trypan Blue dye exclusion) and analyzed for Vβ11 and FOXP3 expression to calculate expansion of viable FOXP3+ Tregs. During the antigenic activation (days 0-3), Tregs expanded ~7-fold while retaining high FOXP3 expression in nearly 100% of the population. Tregs expanded another 4-fold from days 3-6 for a net 26-28 fold expansion since day 0 (FIG. 8, panel F). Importantly, there was no difference in the expansion rates between Tregs cultured in the presence or absence of PC61 immediately following antigenic activation, such that CD25$^{high}$ Tregs were resistant to PC61 antagonism. From days 6-9, Tregs reverted to a quiescent resting phase and did not expand in numbers either with or without PC61. The percentage of FOXP3+ Tregs in each culture remained >98% through the 6 days of IL-2 propagation regardless of the presence or absence of PC61. Overall, in long-term cultures of resting quiescent Tregs (i.e., weeks to months without activation), cell numbers were static or modestly expanded (1-2 fold) over the course of a week. These data provide evidence that 2D2 Tregs can undergo an approximate 26-fold expansion over the course of 9 days following a 3-day cellular activation and 6 days of rest. This activation-rest strategy is based on the classical method for derivation of T cell lines and is also sufficient for expansion of stable FOXP3+ Treg lines.

Although PC61 was deleterious in the initial activation culture (FIG. 2, panel A), PC61 was beneficial in the secondary re-activation cultures (FIG. 8). However, this difference reflected a difference of strategy regarding the initial selection of the line versus the subsequent re-activation and expansion of the line. That is, exogenous IL-2 was not added to primary activations to reinforce antigen specificity of the initial activation, whereas optimization experiments showed that the inclusion of exogenous IL-2 in secondary re-activation promoted expansion of the established clonotypic line. Basically, PC61 preserved the FOXP3 phenotype whenever exogenous IL-2 was added to the culture because unmitigated IL-2 signaling resulted in Tcon dominance and overgrowth/destabilization of the Treg line. Thus, PC61 was beneficial in secondary re-activation cultures because these cultures were supplemented with exogenous IL-2.

Cultured Tregs Exhibited In Vitro and In Vivo Suppressive Activities.

Figure 9:
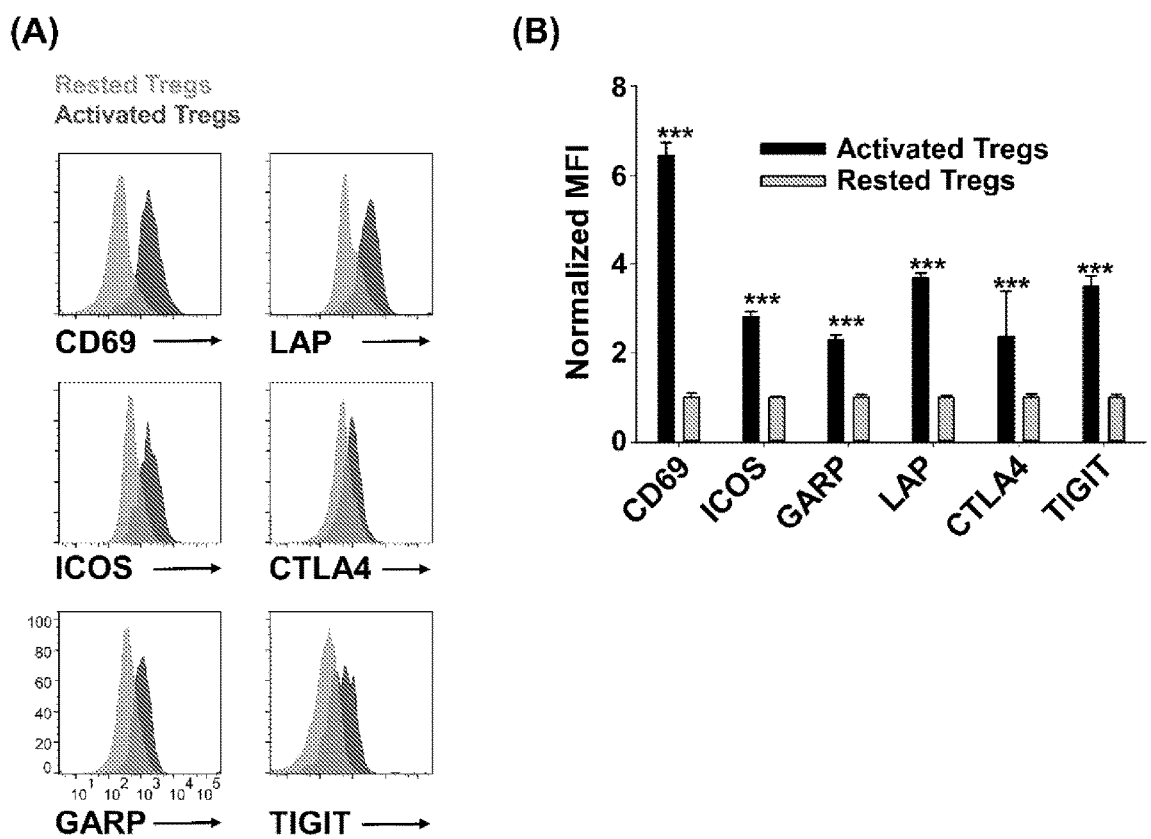
FIG. 9. Reactivated Tregs upregulated Treg-associated activation markers. To generated activated Tregs, 100,000 rested Tregs (>90% FOXP3+) and 10$^6$ irradiated SPL were cultured for 2 days with 1 μM MOG35-55, rat IL-2, and 10 μg/ml PC61. A control rested Treg line was passaged in IL-2 and PC61. Activated Tregs versus rested FOXP3$^+$ Tregs were gated and analyzed for the indicated markers. Representative overlapping histograms are shown in (panel A). Relative MFIs for the indicated markers on gated Tregs are shown in (panel B). MFI values were normalized so that rested Treg MFI values were equal to 1. ***p<0.001. These data are representative of three independent experiments.
Figure 10:
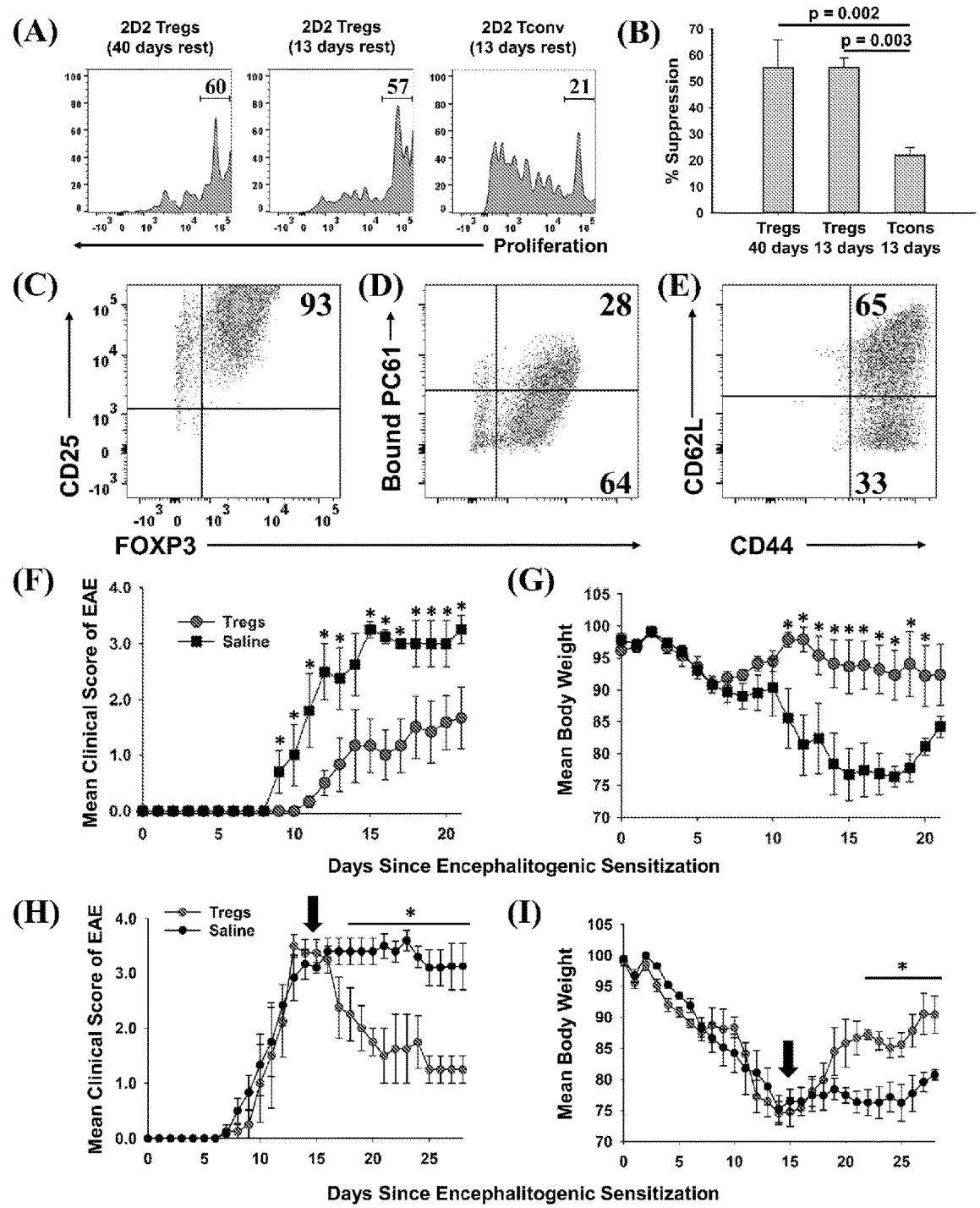
FIG. 10. A 2D2-FIG, MOG-specific FOXP3$^+$ Treg line exhibited in vitro and in vivo suppressive activities. (panels A, B) To prepare Tregs and a control line, CD45.2 2D2-FIG FOXP3$^+$ Tregs were cultured in PC61 and IL-2 for either 13 days or 40 days, and CD45.2 2D2-FIG Tcons were cultured in IL-2 for 13 days. To test the ability of Tregs to suppress naïve T cell activation, 25,000 CD45.2 2D2-FIG Tregs or 25,000 CD45.2 2D2-FIG Tcons were co-cultured with 150,000 CTV-stained CD45.1 2D2-FIG SPL responders for 5 days with 1 µM MOG35-55 and IL-2 (200 µl cRPMI). (panel A) CTV dye dilution and (panel B) percent suppression of CD45.1-gated responder T cells were analyzed by one-way ANOVA (n=3). (panels C-G) A continuous line of FOXP3$^+$ Tregs was activated with irradiated splenic APC, 1 µM MOG35-55, IL-2, and 100 pM TGF-β for 3 days. The PC61 mAb was not added to these cultures to avoid adoptive transfer of antibody-coated T cells. Activated Tregs were cultured one additional day in IL-2 and were analyzed for expression of CD25 (clone 3C7) (panel C), surface-bound PC61 (anti-rat IgG) (panel D), and CD44 and CD62L (panel E). Tregs were extensively washed and injected ($3 \times 10^6$/mouse) into naïve recipients on day −1. Recipients were then challenged with 100 µg MOG35-55 in CFA on day 0 and were given Pertussis toxin on days 0 and 2 to elicit EAE. Significant differences (p <0.05) were noted for the mean daily EAE scores on days 9-13 and 15-21 (panel F) and for daily weight loss on days 11-20. (panels H,I) EAE was elicited by administering 200 µg MOG35-55 in CFA on day 0 and Pertussis toxin on days 0 and 2. At peak disease (day 15, indicated by black arrow), activated 2D2 Tregs ($3 \times 10^6$/mouse) were administered i.v. by retro-orbital injection. Significant differences (p<0.05) were noted for mean daily EAE scores on days 18-28 (panel H) and for daily weight loss on days 21-28 (panel I).

Phenotypic analysis of activated Tregs revealed the activation-dependent upregulation of functional Treg markers including LAP, CTLA4, GARP, and TIGIT (FIG. 9). These data reveal that TGF-β-conditioned activation of Tregs upregulates several markers associated with suppressive Treg function. To determine if continuously-propagated FOXP3+ Tregs have suppressive capabilities, 2D2 Tregs were assayed for in vitro and in vivo suppressive activity. To assess in vitro suppressive activity, CD45.2 2D2 Tregs were cultured for either 40 days or 13 days in IL-2 and PC61 whereas a control CD45.2 2D2 Tcon line was derived by propagation in IL-2 alone for 13 days. These Treg and control lines were then cultured with CTV-stained naïve responders from CD45.1 2D2 splenic leukocytes in the presence of MOG and IL-2 (FIG. 10, panel A). CTV dilution was measured in the CD45.1+ responders after 5 days as a measure of T cell proliferation. Suppressive activity was based on the percentages of hypo-proliferative CD45.1 2D2 T cells (FIG. 10, panel B). Responder 2D2 T cell proliferation was significantly inhibited by the presence of 2D2 Tregs when compared to cultures containing the 2D2 Tcon line. There was no difference in suppressive activities of Tregs rested for 40 days or 13 days. These data provide evidence that Treg function is maintained when Tregs are continuously cultured with IL-2 and PC61.

A central question was whether these Tregs, representing the 2D2 MOG35-55-specific clonotype, exhibited suppressive activity in adoptive transfer experiments. To address this question, a continuous line of FOXP3+ Tregs was activated with irradiated splenic APC, 1 μM MOG35-55, IL-2, and 100 pM TGF-β for 3 days but without PC61 mAb to avoid coating the T cells with a rat IgG1 mAb that had depleting activity in vivo. Cell surface PC61 remained high in the immediate aftermath of the activation culture, and thus the Tregs were cultured overnight in IL-2 to remove more cell-surface CD25/PC61 complexes. Phenotypic analysis of Tregs on the day of transfer showed that 93% were FOXP3$^+$ CD25$^{high}$ Tregs (FIG. 10, panel C). Most of the transferred Tregs had no or low detectable levels of PC61 on the cell surface as determined by staining with anti-rat IgG secondary antibody (FIG. 10, panel D). 65% of Tregs were CD44$^{high}$CD62L$^{high}$, whereas 33% of Tregs were CD44$^{high}$ CD62L$^{low}$ (FIG. 10, panel E). One day after adoptive transfer, mice were actively challenged to elicit EAE. The adoptive transfer of Tregs ameliorated severity of clinical paralysis and EAE-associated loss of body weight (FIG. 10, panels F and G). Recipients of Tregs (n=6) differed from control mice (n=5) in mean cumulative scores (12.2±4.0 versus 26.8±4.6; p=0.0198), mean maximal scores (2.0±0.7 versus 3.6±0.2; p=0.0343), mean maximal weight loss (12.5%±4.4% versus 28.7%±1.1%; p=0.00475), and mean average weight loss (5.7%±3.3% versus 21.5%±2.4%; p=0.00249). Mice that received Tregs had significantly lower mean daily clinical EAE scores on days 9-13 and 15-21 and significantly less weight loss on days 11-20 as assessed by the Student t test. These data provided evidence that PC61 enables the selection of immunosuppressive FOXP3$^+$ CD25$^{high}$ Tregs that when appropriately activated have the ability to inhibit EAE in adoptive transfer experiments.

To address the Treg adoptive immunotherapy in a relevant pre-clinical model, adoptive transfer of activated FOXP3$^+$ Tregs was performed in mice that were exhibiting severe paralytic EAE (FIG. 10, panels H, I). Mice were actively challenged with MOG35-55 in CFA to induce EAE on day 0 and then were separated into two groups that were matched for EAE severity and weight loss on day 15. Blastogenic FOXP3$^+$ Tregs were previously prepared by activation for 3 days with irradiated bone marrow-derived dendritic cells, Con-A, MOG35-55, IL-2, Vitamin C, and TGF-β. These activation cultures were supplemented with Vitamin C due to the emerging awareness that the vitamin acts to promote functionality and stability to effector Tregs (Sasidharan Nair V, et al. *J Immunol* (2016) 196(5):2119-31. doi: 10.4049/jimmunol.1502352. PubMed PMID: 26826239; Yue X, et al. *J Exp Med* (2016) 213(3):377-97. doi: 10.1084/jem.20151438. PubMed PMID: 26903244; PubMed Central PMCID: PMC4813667; Kasahara H, et al. *Int Immunol* (2017). Epub 2017/11/11. doi: 10.1093/intimm/dxx060. PubMed PMID: 29126272; Nikolouli E, et al. *Front Immunol* (2017) 8:748. Epub 2017/07/14. doi: 10.3389/fimmu.2017.00748. PubMed PMID: 28702031; PubMed Central PMCID: PMCPMC5487376; Someya K, et al. *Int Immunol* (2017) 29(8):365-75. Epub 2017/10/20. doi: 10.1093/intimm/dxx049. PubMed PMID: 29048538). Approximately 97% of cells expressed high levels of FOXP3, and these blastogenic Tregs had low to no detectable PC61. Adoptive transfer of these Tregs significantly alleviated severity of EAE based on a decrease in mean clinical score and an increase in body weight. When analyzed from days 20-28, mice that received Tregs (n=4) differed from control mice (n=5) in mean cumulative scores (13.3±3.3 versus 28.4±1.7; p=0.003), mean maximal scores (2.1±0.5 versus 3.8±0.2; p=0.0035), mean maximal weight loss (19.7%±0.9% versus 27.3%±2.2%; p=0.0103), and mean average weight loss (12.7% 0.9% versus 22.8%±1.7%; p=0.00102). The transfer of Tregs significantly alleviated the severity of EAE based on a decrease in mean daily clinical scores from days 18-28 and an increase in body weight from days 22-28. These data provided evidence that blastogenic 2D2 Tregs can mitigate EAE when administered in a therapeutic treatment regimen.

Like the Bivalent PC61 mAb, a Monovalent PC61scFv Promoted the Dominant Outgrowth of FOXP3$^+$ Tregs in Mixed Cultures.

We derived an expression system for a single-chain fragment variable (scFv) version of PC61 to assess whether a monovalent non-signaling version of PC61 retained Treg-stabilizing ability. This PC61scFv protein has the same binding specificity as PC61 (anti-CD25). However, unlike the intact PC61 mAb, PC61scFv was monovalent and therefore lacked cross-linking activity necessary for signaling. The PC61scFv also lacked constant region heavy chain domains and therefore lacked interactions with complement and FcγR. The PC61scFv is believed to have qualitative advantages over intact PC61 in regard to tissue penetrance and absence of in vivo depleting activity. We tested the ability of this monomeric PC61scFv to stabilize Tregs in short-term cultures in comparison to the PC61 mAb (FIG. 11). 2D2-FIG Tregs were activated with MOG35-55 in the presence of TGF-β for 3 days before being passaged into media containing IL-2 along with 65 nM PC61scFv, 65 nM PC61 mAb, or vehicle. Cells were passaged under the same conditions every 3-4 days. The presence of PC61scFv resulted in high Treg percentages (85% on day 14) indicating that PC61scFv mimicked the effect of PC61 mAb in vitro (FIG. 11, panels A and B). PC61scFv was slightly less efficient compared to the intact PC61 mAb, although this minor difference most likely was due to the lower affinity associated with monovalent binding, in contrast to the bivalent interactions of intact PC61 with CD25. The specificity of PC61scFv was confirmed by the ability of surface-bound PC61scFv to block the binding of a fluorochrome-conjugated PC61 mAb (FIG. 11, panel C). These data indicate that PC61 mediates Treg stabilization via CD25 neutralization rather than CD25 crosslinking.

DISCUSSION

Stable growth of autoreactive, TGF-β-induced FOXP3$^+$ Tregs represents a critical prerequisite for effective Treg adoptive immunotherapies of autoimmunity and chronic inflammatory disease. However, the lack of viable strategies to maintain and expand functional CD25$^{high}$ FOXP3$^+$ Tregs in sustained culture has severely limited progress. Solutions to this problem represent a critical unmet need. The main issue is that FOXP3 expression in some Tregs wanes on a per cell basis over time, and otherwise stable FOXP3$^+$ Tregs are overgrown by conventional T cells when cultured in IL-2, such that the cultured T cell population may acquire immune effector functions rather than suppressive regulation activity. This study provides a solution to this problem. Addition of the anti-mouse CD25 antibody PC61 to a mixed culture of TGF-β-induced Tregs and Tcons in the presence of IL-2 led to the rapid establishment of cultures dominated by Tregs (>90% Tregs). This approach did not depend upon genetic modification or physical purification. These Treg lines indefinitely sustained a Treg lineage phenotype when maintained with low concentrations of IL-2 and high concentrations of PC61 in continuous culture. The Tregs derived in this study actively expanded and remained stable in the presence of PC61 and TGF-β in antigen-induced reactivation cultures, such that blastogenic Tregs expressed the prototypic Treg markers together with suppressive activity in vitro and in vivo.

Elevated CD25 Expression on Mature Tregs Provides an Exploitable Treg Window.

Previous studies showed that the potent IL-2 responsiveness of Tregs can be used to selectively promote Treg responses. For example, low-dose IL-2 therapies for Type 1 Diabetes selectively expanded existing Treg populations which could suppress islet cell destruction (Bluestone J A, et al. *Sci Transl Med* (2015) 7(315):315ra189. doi: 10.1126/scitranslmed.aad4134. PubMed PMID: 26606968; PubMed Central PMCID: PMC4729454). Additionally, anti-IL-2 mAb/IL-2 immune complexes may target IL-2 to different T cell subsets depending on the epitope specificity of the anti-IL-2 mAb in the complex (Boyman O, et al. *Science* (2006) 311(5769):1924-7. doi: 10.1126/science.1122927. PubMed PMID: 16484453; Letourneau S, et al. *Proc Natl Acad Sci USA* (2010) 107(5):2171-6. doi: 10.1073/pnas.0909384107. PubMed PMID: 20133862; PubMed Central PMCID: PMC2836659; and Spangler J B, et al. *Immunity* (2015) 42(5):815-25. doi: 10.1016/j.immuni.2015.04.015. PubMed PMID: 25992858; PubMed Central PMCID: PMC4439582). The JES6-1 anti-IL-2 mAb/IL-2 immune complex appeared to target IL-2 to Tregs to favor Treg expansion. Conversely, the S4B6 anti-IL-2 mAb/IL-2 complex favorably expanded effector T cells by blocking the interaction between IL-2 and CD25. Advantages of targeting IL-2 versus CD25 have yet to be directly compared although targeting CD25, the Treg-specific component of the IL-2 receptor, may have qualitative advantages given the wide variations in endogenous IL-2 concentrations that may exist during chronic inflammatory autoimmune disease. Blockade of CD25 may constrain IL-2 signaling across a broad IL-2 concentration range, with an upper threshold defined by those levels of IL-2 sufficient for CD25-independent IL2Rβγ signaling. That is, even with widely varying concentrations of IL-2 and cell surface CD25, mAb-mediated blockade of CD25 may provide a reliable clamp to ensure low-zone IL-2 signaling to promote dominant Treg responses.

The IL-2 concentration was instrumental in determining T cell subset dominance (FIG. 6, panels A and D). Low-intensity and high-intensity IL-2 signaling respectively supported Treg or Tcon subset dominance. The relation between low-zone IL-2 signaling and Treg responses reflected superior CD25 expression and exquisite IL-2 sensitivity of Tregs. The relation between high-zone IL-2 signaling and Tcon subset dominance may reflect differences in the respective IL-2 signaling pathways. IL-2 signaling in Tregs is mediated primarily through the JAK/STAT pathway whereas IL-2 signaling in Tcon subsets is mediated robustly through both JAK/STAT and PI(3)K pathways. PTEN, the PI(3)K inhibitor, is selectively expressed in Tregs and is important in stabilizing the Treg phenotype (Huynh A, et al. *Nat Immunol* (2015) 16(2):188-96. doi: 10.1038/ni.3077. PubMed PMID: 25559257; PubMed Central PMCID: PMC4297515) whereas PTEN is down-regulated in Tcon subsets (Bensinger S J, et al. *J Immunol* (2004) 172(9):5287-96. PubMed PMID: 15100267; PubMed Central PMCID: PMC2842445). Thus, IL-2 has superior potency for Tregs due to higher CD25 expression, which confers Treg dominance at low IL-2 concentrations. In contrast, IL-2 has superior efficacy for Tcons due to robust signaling through both JAK/STAT and PI(3)K pathways, which confers Tcon dominance at high IL-2 concentrations. Thus, differential expression of CD25 and PI(3)K signaling pathways provide qualitative distinctions in IL-2 signaling pathways that are foundational for the specialized Treg and Tcon niches.

Chronic CD25 blockade was the key to exploitation of the Treg window and stabilization of FOXP3$^+$ Tregs. However, anti-CD25 mAbs varied substantially in Treg stabilization activity. The mAb of choice for stabilization of mouse Tregs was PC61, which was a stronger inhibitor of IL-2-dependent proliferation than the anti-CD25 mAbs 3C7 and 7D4 (FIG. 5, panel A). The use of PC61 in concert with low IL-2 concentrations provided the appropriate qualitative and quantitative signals necessary for stabilization of FOXP3 expression and maintenance of the Treg phenotype. Although PC61 was not useful in initial activation of 2D2-FIG SPL with antigen and TGF-β, PC61 in concert with IL-2 was included in all subsequent cultures including maintenance cultures and re-activation cultures. TGF-β was beneficial during the initial activation culture and in all subsequent re-activation cultures. Thus, PC61 worked in concert with IL-2 to maintain Tregs, and TGF-β worked in concert with MHCII-restricted antigen to stabilize Tregs during blastogenic expansion. PC61 was the technical tool that allowed exploitation of a Treg window, which was operationally defined by a low range of IL-2 signaling that enabled dominant outgrowth of stable FOXP3$^+$ Tregs. If IL-2 concentrations in PC61-supplemented cultures exceeded this range, then PC61 lacked Treg stabilization activity, and Tcon subsets dominated the culture.

An important consideration was whether PC61 mAb crosslinked CD25 would elicit qualitatively-unique, non-canonical IL-2 signaling pathways to stabilize Tregs. CD25 has no known intracellular signaling activity, and IL-2 signaling is mediated through the cytoplasmic domains of CD122 and CD132 (Boyman O, Sprent J. *Nat Rev Immunol* (2012) 12(3):180-90. Epub 2012/02/22. doi: 10.1038/nri3156. PubMed PMID: 22343569). Nonetheless, CD25 has a cytoplasmic domain, and CD25 crosslinking may indirectly crosslink other associated proteins. Hence, our studies with intact PC61 mAb could not exclude the possibility that PC61 may qualitatively modulate IL-2 signaling to favor the Treg subset. To address this question, we derived a monomeric PC61scFv that lacked cross-linking activity. This monomeric PC61scFv had essentially the same activity as PC61 mAb in Treg stabilization assays (FIG. 11). These results support the conclusion that PC61 stabilizes Tregs primarily through preferential blockade of IL-2 signaling in Tcon subsets. Notably, the use of PC61 or PC61scFv was fully sufficient for derivation of long-term stable FOXP3$^+$ Treg lines without any physical purification or genetic modification. The use of suitable anti-CD25 reagents could be used to guide formulation of culture conditions suitable for derivation of enriched Treg populations in large culture settings or bioreactors.

Low-Zone IL-2 Signaling Confers Treg Stability.

The IL-2 pathway is critical for self-tolerance in that genetic deficiencies in the major components of the IL-2/CD25/IL2Rβγ/STAT5/JAK3 pathway result in systemic autoimmunity (O'Shea J J, *Nat Rev Immunol* (2002) 2(1):37-45. Epub 2002/03/22. doi: 10.1038/nri702. PubMed PMID: 11905836; Sadlack B, *Cell* (1993) 75(2):253-61. Epub 1993/10/22. PubMed PMID: 8402910; Sharfe N, et al. *Proc Natl Acad Sci USA* (1997) 94(7):3168-71. Epub 1997/04/01. PubMed PMID: 9096364; PubMed Central PMCID: PMCPMC20340; Malek T R, et al. *Immunity* (2002) 17(2):167-78. Epub 2002/08/28. PubMed PMID: 12196288; Teglund S, et al. Stat5a and Stat5b proteins have essential and nonessential, or redundant, roles in cytokine responses. Cell (1998) 93(5):841-50. Epub 1998/06/18. PubMed PMID: 9630227; Antov A, et al. *J Immunol* (2003) 171(7):3435-41. Epub 2003/09/23. PubMed PMID: 14500638). The paradox is that IL-2 is the prototype T cell growth factor in vitro that drives dominant outgrowth of CD4+ and CD8+ effector lineages. Several studies showed that IL-2 is required for induction and maintenance of FOXP3 expression in Tregs (Malek T R, Castro I. *Immunity* (2010) 33(2):153-65. doi: 10.1016/j.immuni.2010.08.004. PubMed PMID: 20732639; PubMed Central PMCID: PMC2946796), but IL-2 also drives proliferation of Tcons and destabilization of Treg populations (FIGS. 2 and 6). This study provides insight into the "IL-2 paradox" by showing that continuous culture of Tregs in IL-2 and PC61 resulted in maintenance of high levels of FOXP3 expression and Treg stability for more than 60 days without any phenotypic or functional attenuation (FIG. 7). Indeed, continuous culture in IL-2 and PC61 appeared to promote a canonical Treg phenotype as measured by progressive increases in the expression of Helios and Neuropilin-1 (FIG. 7). These findings provide suggestive evidence that the duration of a Treg phenotype might be associated with progressive stabilization of a FOXP3+ Treg phenotype, such that Tregs may gravitate to a more differentiated phenotype with time. If continuous low-zone IL-2 signaling in the context of a Treg window is key for understanding stabilization of FOXP3+ Tregs in vitro, the implication is that continuous low-zone IL-2 signaling may also be key for maintenance and progressive differentiation of Tregs in vivo.

TGF-β was also required for Treg stability, but only in the context of MHCII-restricted antigen presentation by splenic APC in activation-dependent expansion cultures. TGF-β had no effect in maintenance cultures when added during propagation in IL-2 with or without PC61. In re-activation cultures, a TGF-β-blocking antibody led to accelerated Treg destabilization, whereas addition of exogenous TGF-β preserved FOXP3 expression and FOXP3+ Treg percentages at optimal levels (FIG. 8). In re-activation cultures that included IL-2 and TGF-β, Tregs expanded more than 5-fold without loss of FOXP3 as both a percentage of the T cell population and on a per cell basis based on MFI. The concentration of TGF-β in the reactivation culture was tailored to the TCR strength for cognate antigen of the particular clonotype. In other words, the correct balance of TGF-β, antigen, and IL-2 was necessary for optimal expansion of Tregs and maintenance of the Treg phenotype. For example, 100 pM TGF-β was sufficient for expansion of stable MOG-specific Tregs, which represents a low affinity clonotype. Higher concentrations of TGF-β (1 nM) were needed for optimal expansion of stable OVA-specific Tregs, which exhibits much stronger antigenic potency. Thus, TGF-β was needed in sufficient concentrations to counterbalance antigenic strength but these TGF-β concentrations had to be below thresholds that completely blocked the antigenic response. Thus, like the Treg window established for PC61/IL-2 in maintenance cultures, an appropriate range of TGF-β concentrations was needed for optimal stabilization of Tregs during antigen-reactivated expansion cultures.

For both IL-2 and PC61 in maintenance cultures and TGF-β in reactivation cultures, a major question was whether Treg stabilization reflected the intrinsic stabilization of FOXP3 expression or whether differential growth (or death) rates in Treg and Tcon subsets determined final Treg percentages. The most likely scenario is that both mechanisms contributed in part to the derivation of continuous Treg lines. For example, Tregs cultured in the presence of PC61 and IL-2 had higher FOXP3 expression on a per cell basis than Tregs cultured in IL-2 alone, and Tregs cultured in PC61 and IL-2 also had higher growth rates than the Tcon subsets. PC61 may suppress Tcon proliferation which in turn may suppress secretion of pro-inflammatory cytokines that could antagonize TGF-β and destabilize FOXP3. These considerations may reflect a fundamental competition between these T cell subsets, wherein Treg subsets inhibit Tcon subsets, and Tcon subsets inhibit Treg subsets via mechanisms of reciprocal inhibition.

An important caveat is that this study pertains to the MOG-specific 2D2 clonotype, the OVA-specific OTII clonotype, and mitogen-activated polyclonal C57BL/6 T cells. The kinetics by which PC61 selects for $CD25^{high}$ Tregs will be determined in part by the relative proportion and persistence of $CD25^{high}$ Treg and Tcon subsets in the cell preparation, which may vary in different T cell preparations. Although PC61/IL-2 selection exploits qualitative distinctions in CD25 expression in Treg and Tcon subsets, stronger antigenic or mitogenic stimuli may cause more persistent CD25 expression in Tcon subsets which may necessitate longer periods of PC61/IL-2 selection to achieve FOXP3+ Treg dominance. PC61-mediated Treg selection therefore may vary in kinetics based on the inherent antigenic reactivity of the relevant clonotype. A second caveat is that PC61/IL-2 selects $CD25^{high}$ FOXP3+ subsets at the expense of $CD25^{low}$ FOXP3+ subsets. For example, pre-existing Tregs isolated from secondary lymphoid organs express CD25 across a quantitative continuum, and PC61/IL-2 selects the $CD25^{high}$ subset that represents the functionally mature suppressive subset.

This study defined an operative 'Treg niche' defined by low-zone IL-2 signaling. This study also provided a strategy for maintenance and expansion of stable FOXP3+ Treg lines in vitro, which could be propagated indefinitely without phenotypic instability. These principles were validated for TGF-β-inducible Tregs, which may be optimal for derivation of antigen-specific Tregs from peripheral blood. While not wishing to be bound to any particular theory, we believe that these principles would also apply to thymic or natural tTreg/nTregs. Overall, this strategy could be applied broadly to Tregs of any clonotypic specificity and thereby may have applicability for the advancement of antigen-specific Treg-based immunotherapies.

While there are shown and described exemplary embodiments of the invention, it is to be understood that the invention is not limited thereto but may be otherwise variously embodied and practiced within the scope of the following claims. Since numerous modifications and alternative embodiments of the present invention will be readily apparent to those skilled in the art, this description is to be construed as illustrative only and is for the purpose of teaching those skilled in the art the best mode for carrying out the present invention. Accordingly, all suitable modifications and equivalents may be considered to fall within the scope of the following claims.

That which is claimed:

1. An in vitro method of preparing a regulatory T-cell (Treg) population comprising:
    exposing T-cells to a medium comprising an anti-inflammatory cytokine and an anti-inflammatory cytokine receptor inhibitor; and
    propagating the T-cells in the medium comprising the anti-inflammatory cytokine and the anti-inflammatory cytokine receptor inhibitor to provide the Treg population, wherein the anti-inflammatory cytokine is IL-2 and the anti-inflammatory cytokine receptor inhibitor is an anti-CD25 antibody and/or a fragment thereof.

2. The in vitro method of claim 1, further comprising, prior to the exposing step, activating the T-cells to provide activated T-cells, and wherein the exposing step comprises:
    exposing the activated T-cells to the medium comprising the anti-inflammatory cytokine and the anti-inflammatory cytokine receptor inhibitor.

3. The method of claim 1, wherein the T-cells are naïve T-cells.

4. The in vitro method of claim 2, wherein the T-cells are activated in the presence of TGF-β and/or IFN-β.

5. The in vitro method of claim 2, wherein the T-cells are activated in the presence of an antigen, a superantigen, and/or a mitogenic stimulus.

6. The in vitro method of claim 1, wherein the Treg population is an antigen-specific Treg population.

7. The in vitro method of claim 1, wherein the Treg population comprises FOXP3$^+$ Tregs.

8. The in vitro method of claim 1, wherein the Treg population comprises CD4$^+$CD25$^+$FOXP3$^+$ Tregs.

9. The in vitro method of claim 1, wherein the Treg population comprises Tregs expressing Nrp1 and/or Helios.

10. The in vitro method of claim 1, wherein the concentration of the anti-inflammatory cytokine is in a range of about 1 pM to about 10 nM.

11. The in vitro method of claim 1, wherein the concentration of the anti-inflammatory cytokine receptor inhibitor is in a range of about 1.0 µg/ml to about 32 µg/ml.

12. The in vitro method of claim 1, wherein the anti-CD25 antibody and/or fragment thereof is an anti-human CD25 antibody and/or a fragment thereof.

13. The method of claim 1, further comprising a step of administering a therapeutic amount of the Treg population to a subject in need thereof.

14. The method of claim 13, wherein the administering elicits a tolerogenic response in the subject.

15. An in vitro method of maintaining a Treg population comprising:
    maintaining the Treg population prepared according to claim 1 in the presence of the anti-inflammatory cytokine and the anti-inflammatory cytokine receptor inhibitor.

16. The in vitro method of claim 1, wherein the anti-CD25 antibody and/or fragment thereof binds human CD25.

* * * * *

UNITED STATES PATENT AND TRADEMARK OFFICE
CERTIFICATE OF CORRECTION

PATENT NO. : 11,384,336 B2
APPLICATION NO. : 16/465773
DATED : July 12, 2022
INVENTOR(S) : Wilkinson et al.

It is certified that error appears in the above-identified patent and that said Letters Patent is hereby corrected as shown below:

In the Specification

Column 8, Line 39: Please correct "+10%, +5%," to read --± 10%, ± 5%,--

Column 8, Line 40: Please correct "+1%," to read --±1%,--

Column 8, Line 43: Please correct "0.5%," to read --±0.5%,--

Column 12, Line 11: Please correct "k monoclonal" to read --κ monoclonal--

Column 12, Line 13-14: Please correct "K monoclonal" to read --κ monoclonal--

Column 12, Line 57: Please correct "+20%" to read --±20%--

Column 18, Line 15: Please correct "TGF-(3-induced" to read --TGF-(β-induced--

Column 25, Line 21: Please correct "FOXP3′′′′" to read --FOXP3 ̅--

Column 29, Line 64: Please correct "12.7% 0.9%" to read --12.7% ± 0.9%--

Signed and Sealed this
Eleventh Day of April, 2023

*Katherine Kelly Vidal*
Katherine Kelly Vidal
*Director of the United States Patent and Trademark Office*